United States Patent
Zhang

(10) Patent No.: US 9,593,335 B2
(45) Date of Patent: Mar. 14, 2017

(54) SMALL INTERFERENCE RNAS, USES THEREOF AND METHOD FOR INHIBITING THE EXPRESSION OF PLK1 GENE

(71) Applicant: SUZHOU RIBO LIFE SCIENCE CO., LTD., Kunshan (CN)

(72) Inventor: Hongyan Zhang, Kunshan (CN)

(73) Assignee: SUZHOU RIBO LIFE SCIENCE CO., LTD., Kunshan (CN)

( * ) Notice: Subject to any disclaimer, the term of this patent is extended or adjusted under 35 U.S.C. 154(b) by 0 days.

(21) Appl. No.: 15/130,091

(22) Filed: Apr. 15, 2016

(65) Prior Publication Data

US 2016/0289687 A1 Oct. 6, 2016

Related U.S. Application Data

(62) Division of application No. 14/353,017, filed as application No. PCT/CN2012/083195 on Oct. 19, 2012, now Pat. No. 9,328,348.

(30) Foreign Application Priority Data

Oct. 19, 2011 (CN) .......................... 2011 1 0319067

(51) Int. Cl.
*C12N 15/11* (2006.01)
*C12N 15/113* (2010.01)

(52) U.S. Cl.
CPC ...... *C12N 15/1137* (2013.01); *C12N 15/1135* (2013.01); *C12Y 207/11021* (2013.01); *C12N 2310/14* (2013.01); *C12N 2310/321* (2013.01); *C12N 2310/322* (2013.01); *C12N 2320/30* (2013.01)

(58) Field of Classification Search
CPC ............ C12N 15/1137; C12N 2310/14; C12N 2310/32
See application file for complete search history.

(56) References Cited

U.S. PATENT DOCUMENTS

| 7,598,370 B2 | 10/2009 | Khvorova et al. |
| 2010/0004141 A1 | 1/2010 | Khvorova et al. |
| 2011/0045080 A1 | 2/2011 | Powis et al. |

FOREIGN PATENT DOCUMENTS

| CN | 1651450 | 8/2005 |
| CN | 102102101 | 6/2011 |
| WO | 2009/082817 | 7/2009 |

OTHER PUBLICATIONS

Yang et al. "Systemic delivery of siRNA with cationic lipid assisted PEG-PLA nanoparticles for cancer therapy." J. of Controlled Release, 2011, doi:10.1016/j.jconrel.2011.07.035.
Sun et al. "Small interfering RNA-mediated knockdown of polo-like kinase 1 promotes apoptosis in human hepatocellular carcinoma cell line BCL-7402." World Journal of Gastroenterology, 2011, 9, 28, 19(27), 2822-2828.
"Supreme Court decision might strengthen biomarker patents." Nature, Aug. 2010, vol. 9, 586-587.
Cucchi et al. "Phosphorylation of TCTP as a Marker for Polo-like Kinase-1 Activity In Vivo" Anticancer Research 30:4973-4986 (2010).

*Primary Examiner* — Brian Whiteman
(74) *Attorney, Agent, or Firm* — Nixon Peabody LLP

(57) ABSTRACT

The present invention provides siRNAs for inhibiting the expression of plk1 gene, and the method for inhibiting the expression of plk1 gene in mammalian cells. The siRNAs of the present invention have the double-stranded structure, and said double-stranded structure is composed of the first single strand and the second single strand that are fully complementary, wherein the sequence of said first single strand is the same as the target sequence within the sequence as shown in SEQ ID NO: 1, and the sequence of said second single strand is complementary to the target sequence within the sequence as shown in SEQ ID NO: 1. The siRNAs of the present invention can sequence specifically mediate the inhibition of plk1 gene expression, and have a good serum stability. By the introduction of the siRNAs of the present invention into the tumor cells, the expression of plk1 gene can be effectively inhibited, and the growth of tumor cells is inhibited and the apoptosis of tumor cells is promoted.

9 Claims, 3 Drawing Sheets

SMALL INTERFERENCE RNAS, USES THEREOF AND METHOD FOR INHIBITING THE EXPRESSION OF PLK1 GENE

CROSS-REFERENCE TO RELATED APPLICATIONS

This application is a Divisional Application of U.S. application Ser. No. 14/353,017, filed Apr. 18, 2014, which is a U.S. national stage of PCT/CN2012/083195, filed on Oct. 19, 2012 which claims priority to Chinese Patent Application No. 201110319067.8, filed on Oct. 19, 2011, the contents of which are each incorporated herein by reference in their entirety.

SEQUENCE LISTING

The sequence listing of the present application has been submitted electronically via EFS-Web as an ASCII formatted sequence listing with a file name "USSN14353017_Sequence_Listing", creation date of Mar. 29, 2016 and a size of 70,856 bytes. The sequence listing submitted via EFS-Web is part of the specification and is herein incorporated by reference in its entirety.

FIELD OF THE INVENTION

The present invention relates to a siRNA, uses thereof and a method for inhibiting the expression of plk1 gene. To be specific, the present invention relates to a siRNA which inhibits the expression of plk1 gene and uses thereof, as well as a method for inhibiting the expression of plk1 gene by using a siRNA.

BACKGROUND OF THE INVENTION

Polo-like kinase-1 (plk1) is a highly conserved serine/threonine kinase. Human plk1 gene is located at position 16p12 of the chromosome, encoding an mRNA of about 2.3 kb, and the molecular weight of the corresponding protein is about 67 kd. plk1 protein has a highly conserved catalytic domain at its N-terminal, and typically has three conserved domains called polo boxes at its C-terminal. The research indicates that plk1 plays a role in inducing DNA synthesis, checking and repairing DNA integrity, and preventing cell apoptosis. plk1 can also inhibit the transcriptional activity of p53 through phosphorylation, and further inhibit p53 from playing the functions of check-point protein and inducing cell apoptosis. p53 is a primary regulatory protein in G1 phase. The inhibitory effect of plk1 on cancer suppressor gene p53 induces continuous, even permanent G1 phase arrest. Further, plk1 is closely related to the occurrence and development of tumors. After the expression of plk1 gene is inhibited, cell proliferation will be inhibited and cell apoptosis will be promoted, thus tumor growth will be inhibited. plk1 can also regulate the inductive production of interferon (IFN) by inhibiting MAVS, thereby disrupting innate immunity.

plk1 highly expresses in most human tumor tissues, including breast cancer, liver cancer, lung cancer and colon cancer. The high expression of plk1 has a statistical correlation with the survival rate of tumor patients, and the expression level of plk1 in tumor tissues is also closely related to tumor metastasis and prognosis, which indicates that plk1 may play an important role during the generation and development of tumors and is a potential target site of antitumor drugs. Research progress also indicates that, blocking the expression of plk1 or inhibiting its kinase activity may effectively inhibit proliferation of tumor cells and mediate their apoptosis, while no obvious impact is exerted on normal cells. At present, a plurality of plk1 inhibitors in preclinical or clinical trial stage all exhibit characteristics of high drug properties and low toxicity.

Breast cancer is one of the most popular malignant tumors among women. Surgery, radiotherapy, chemotherapy and endocrinotherapy are four major clinical treatment means for breast cancer. Regarding most breast cancer patients, cancer cells may have already migrated to other tissues when breast cancer is determined during preliminary diagnosis, while chemotherapy as an important systemic intervention means plays an extremely important role in the treatment of breast cancer. At present, chemotherapeutic means mainly uses small molecular drugs and targeted macromolecular drugs. However, drug potency and consequent drug resistance are two major problems confronting the small molecular drugs commonly used during treatment of breast cancer, while a narrow range of applicable people is a major problem confronting targeted macromolecular drugs. Therefore, small interfering nucleic acid that can inhibit the expression of cancer gene as a substitute drug hopefully may solve the problems that cannot be solved by small molecular drugs and targeted antibody drugs. From several aspects including improvement of treatment effectiveness, drug resistance as well as reduction of toxic and side effect of antitumor drugs, the development of effective siRNA drugs, which are new pharmaceutical molecules that functions in a manner completely different from the action mechanisms of those mainstream drugs currently used in clinical application, has become an urgent need for current clinical application.

SUMMARY OF THE INVENTION

The object of the present invention is to provide a siRNA for inhibiting the expression of plk1 gene, a pharmaceutical composition containing the siRNA as a pharmaceutically active ingredient, a method for inhibiting the expression of plk1 gene using the siRNA or the pharmaceutical composition, and use of the siRNA or the pharmaceutical composition in treatment and/or prevention of cancer diseases.

That is, the present invention achieves the foregoing object by providing the following technical solutions:

In one aspect, the present invention provides a siRNA with a double-stranded structure, the double-stranded structure consisting of a first single strand and a second single strand which are completely complementary, wherein the first single strand has a nucleotide sequence represented by SEQ ID NOs: 2-133 respectively, which is the same as a target site sequence in a plk1 mRNA sequence represented by SEQ ID NO: 1; and the second single strand complementary to the first single strand has a nucleotide sequence represented by SEQ ID NOs: 134-265 respectively, which is complementary to the target site sequence in the plk1 mRNA sequence represented by SEQ ID NO: 1.

According to one embodiment of the present invention, the first single strand has a nucleotide sequence represented by SEQ ID NOs: 4, 17, 38, 42, 55, 65, 66, 68, 77, 93, 103, 104, 109 or 129 respectively, which is the same as a target site sequence in the plk1 mRNA sequence represented by SEQ ID NO: 1; and the second single strand complementary to the first single strand has a nucleotide sequence represented by SEQ ID NOs: 136, 149, 170, 174, 187, 197, 198, 200, 209, 225, 235, 236, 241 or 261 respectively, which is complementary to the target site sequence in the plk1 mRNA sequence represented by SEQ ID NO: 1.

According to one preferred embodiment of the present invention, the first single strand has a nucleotide sequence represented by SEQ ID NOs: 66, 68 or 77 respectively, which is the same as a target site sequence in the plk1 mRNA sequence represented by SEQ ID NO: 1; and the second single strand complementary to the first single strand has a nucleotide sequence represented by SEQ ID NOs: 198, 200 or 209 respectively, which is complementary to the target site sequence in the plk1 mRNA sequence represented by SEQ ID NO: 1.

According to another embodiment of the present invention, the 3'-end of at least one single strand of the first single strand and the second single strand may be attached with 1-3 nucleotides, such that after the first single strand and the second single strand complementarily form the double-stranded structure, a 3' protruding end consisting of the 1-3 nucleotides forms at at least one end of the double-stranded structure, wherein the 3' protruding end preferably consists of two consecutive deoxy-thymidine monophosphates (dTMP) dTdT or two consecutive uridine monophosphates (UMP) UU.

According to another embodiment of the present invention, each of the first single strand and the second single strand contains at least one modified nucleotide group respectively, wherein the modified nucleotide group is a nucleotide group in which at least one of phosphate group, ribose group or base is modified. Preferably, the modified nucleotide group is a nucleotide group in which the 2'-hydroxy of the ribose group is substituted by methoxy or fluorine.

In another aspect, the present invention provides a pharmaceutical composition containing the siRNA which inhibits the expression of plk1 gene as a pharmaceutically active ingredient, as well as a cationic ingredient, a non-cationic ingredient and a pharmaceutically acceptable carrier.

According to one embodiment of the present invention, the cationic ingredient is at least one selected from the group consisting of N,N-dihydroxyethyl-N-methyl-N-2-(cholesteryloxycarbonylamino) ethylammonium bromide, (2,3-dioleoyloxypropyl) trimethylammonium chloride, N-(1-(2,3-dioleoyloxy)propyl)-N,N,N-trimethylammonium chloride, polyethylenimine, poly β-amino ester and chitosan quaternary ammonium salt; the non-cationic ingredient is at least one selected from the group consisting of polyethylene glycol-polylactic acid diblock copolymer, polyethylene glycol-polylactic acid triblock copolymer, polyethylene glycol-poly(lactic acid-glycolic acid) diblock copolymer and polyethylene glycol-poly(lactic acid-glycolic acid) triblock copolymer; and the pharmaceutically acceptable carrier is selected from the group consisting of phosphate buffer solution (PBS) with a pH of 4.0-9.0, tris(hydroxymethyl) aminomethane hydrochloride buffer solution with a pH of 7.5-8.5, normal saline, or 7-15 wt % sucrose solution.

In another aspect, the present invention provides a method for inhibiting the expression of plk1 gene in mammalian cells. This method comprises treatment of introducing the foregoing siRNA into mammalian cells, thereby allowing the siRNA to sequence-specifically induce inhibition of the expression of the plk1 gene.

According to one embodiment of the present invention, the treatment refers to introducing the siRNA directly, or introducing the siRNA in a form of the foregoing pharmaceutical composition containing the siRNA.

In another aspect, the present invention provides use of the foregoing siRNA and pharmaceutical composition in the preparation of drugs for treating and/or preventing tumor, wherein the tumor is breast cancer, liver cancer, lung cancer, cervical cancer or colon cancer with abnormally high expression of plk1 gene.

The siRNA provided by the present invention can sequence-specifically mediate inhibition of the expression of plk1 gene and has desirable serum stability. By introducing the siRNA of the present invention into tumor cells, the expression of endogenous plk1 gene may be effectively inhibited, thereby inhibiting growth of tumor cells and promoting apoptosis of tumor cells.

DETAILED DESCRIPTION OF THE INVENTION

Figure 1:
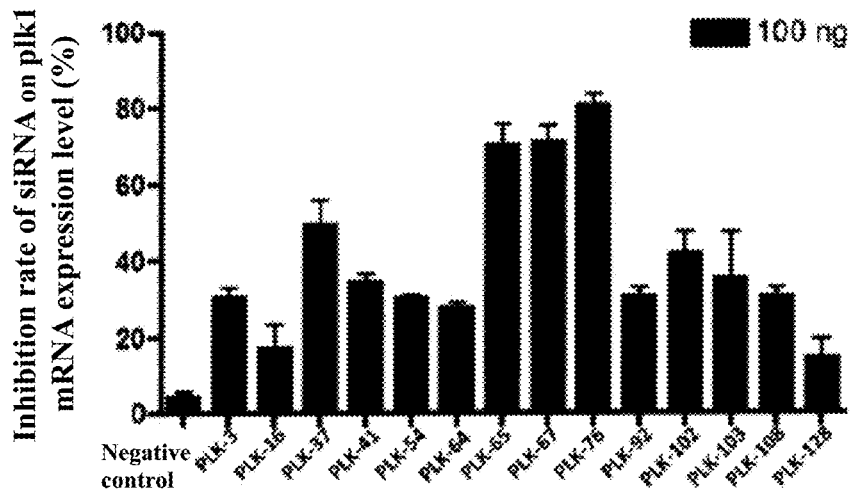
FIG. 1 shows the detection result of the inhibitory effect of the siRNA in Example 2 on the expression level of plk1 mRNA.

The terms used in this specification are defined as follows.

The terms "polo-like kinase 1", "plk1" or "plk1 kinase" refer to a kind of serine/threonine kinase which contains a kinase domain and a polo-box domain. For detailed description of the properties and functions of plk1 kinase, please refer to Nat. Rev. Mol. Cell Biol. 2004, 5:429-. It is known now that the activity and intracellular expression level of plk1 kinase play a critical role in regulating cell mitosis. The plk1 mRNA sequence used in the present invention is the sequence of Genbank accession number NM_005030.3 (SEQ ID NO: 1).

The term "mRNA (messenger RNA)" refers to an RNA molecule which acts as a template for in vivo protein translation transferring gene encoding information from DNA to protein product.

The terms "RNA interference" or "RNAi" refer to a phenomenon of post-transcriptional regulation of gene expression in organisms. This phenomenon is induced by specific degradation of target mRNA mediated by single-stranded or double-stranded RNA. For details of RNAi regulation mechanism, please refer to the descriptions in Biotech. Adv. 2008, 26(3):202- and other literatures.

In the present invention, unless otherwise specified, the terms "small interference/small interfering RNA" or "siRNA" refer to an RNA molecule which can sequence-specifically induce RNAi phenomenon, consists of two single-stranded RNAs with a length of 15-27 nucleotides, and has a partially or completely complementary double-stranded structure. In the siRNA according to the present invention, the length of the complementary double-stranded structure may be 17-25, 18-22 or 19-21 base pairs. The siRNA according to the present invention may be a blunt ended double-stranded RNA structure consisting of two single-stranded RNAs with a length of 15-27 nucleotides, or may also be a structure which has 3' protruding end(s) consisting of 1-3 consecutive nucleotides at at least one end of the double-stranded structure. In the present invention, the 3' protruding end preferably consists of two consecutive deoxy-thymidine monophosphates (dTMP) dTdT or two consecutive uridine monophosphates (UMP) UU.

In the present invention, unless otherwise specified, the terms "first single strand" or "sense strand" refer to one of the two single strands of the siRNA, which has a nucleotide sequence partially or completely the same as the nucleotide sequence of the action site of the siRNA in the target mRNA; while the terms "second single strand" or "antisense strand" refer to the other single strand of the two single strands of the siRNA, which has a nucleotide sequence partially or completely complementary to the nucleotide sequence of the action site of the siRNA in the target mRNA. The first single strand (or sense strand) and the corresponding second single strand (or antisense strand) of the siRNA mentioned in the present invention may form a partially or completely complementary double-stranded structure.

The term "complementary" refers to the circumstance that the bases in two nucleic acid strands form antiparallel complementary pairs according to the base paring principle of guanine G with cytosine C, and adenine A with uracil U/thymine T.

In the present invention, unless otherwise specified, the terms "suppress/suppressing, inhibit/inhibiting" refer to the circumstance that mRNA degradation mediated by siRNA or other small-interfering nucleic acid (siNA) inhibitors results in significant down-regulation of target gene expression. The "significant down-regulation" refers to the circumstance that target gene expression reduces by 5%, 10%, 15%, 20%, 25%, 30%, 35%, 40%, 45%, 50%, 55%, 60%, 65%, 70%, 75%, 80%, 85%, 90%, 95% or 99% or more, or 100% compared with normal level or the level before treatment.

The terms "systemic administration" or "systemic delivery" refer to an administration mode which delivers pharmaceutically active ingredients such as siRNA to a wide range of tissue regions in the body. In order to achieve the effect of systemic administration, it is typically necessary for the pharmaceutically active ingredient or the pharmaceutical composition to have a relatively long blood retention time, and they should not be easily absorbed and cleared by main metabolizing organs such as liver and kidney. As the systemic administration modes of siRNA, intravenous injection, subcutaneous injection, intraperitoneal injection, oral administration and the like may be adopted. In the present invention, systemic administration of siRNA is preferably conducted by intravenous injection.

The terms "local administration" or "local delivery" refer to an administration mode which delivers pharmaceutically active ingredients such as siRNA to local tissue regions. For example, local administration of siRNA may be achieved by directly injecting or applying the pharmaceutically active ingredients such as siRNA in the diseased tissue regions. The tissue regions suitable for local administration of pharmaceutically active ingredients such as siRNA include, for example, organs and tissues such as skin, ocular vitreous cavity, liver, kidney, lung and the like.

In the present invention, the design of siRNA is carried out by using the mRNA sequence of plk1 as a template and selecting a target sequence with a length of 15-27 nucleotides aiming at the conserved region of plk1 gene to obtain the corresponding siRNA. The plk1 mRNA sequence used in the present invention is a sequence of Genbank accession number NM_005030.3 (SEQ ID NO: 1), the length thereof being 2204 nucleotides. The coding region starts from the initiation codon ATG at the $54^{th}$ position and ends at the termination codon TAA at the $1865^{th}$ position. To be specific, the siRNA of the present invention is designed pursuant to the following principles.

First of all, a sequence with a length of 15-27 nucleotides is selected in the full-length sequence range of plk1 mRNA. The sequence with a length of 15-27 nucleotides is selected mainly in accordance with the following principles: 1) The GC content is 35-60%; 2) avoiding locating in a repetitive sequence or low-complex sequence region; 3) avoiding the occurrence of 4 or more consecutive nucleotide sequences; 4) avoiding locating in a sequence region of 50-100 nucleotides containing initiation codon and termination codon of a reading frame. Besides, the composition and thermodynamic property of the nucleotide sequence shall be also analyzed, to ensure that the duplexes can be easily unwound after they enter the body, and immunoreaction shall be avoided. Afterwards, through BLAST analysis, the target site sequences of candidate siRNAs are aligned with human genome sequence in terms of identity to exclude the sequences which have a identity of 16 nucleotides or more with other genes, so as to ensure that the target site sequences of candidate siRNAs do not bear high similarity with the sequences of other irrelevant genes, thereby ensuring that the designed siRNAs merely have specific inhibition effect on the target gene plk1.

In the present invention, the design of siRNA includes the design of the first single strand which is the same as the target site in plk1 mRNA, and the design of the second single strand which is complementary to the target site in plk1 mRNA. In the present invention, the second single strand (or antisense strand) of siRNA is complementary to the target site sequence in the plk1 mRNA sequence, and sequence-specifically induces degradation of plk1 mRNA through RNAi mechanism, thereby resulting in inhibition of the expression of plk1 gene. The first single strand and the second single strand designed by the present invention are completely complementary to each other and may form a double-stranded structure with a blunt end, i.e., without any 3' protruding end, after annealing.

In one embodiment of the present invention, two deoxy-thymidine monophosphates (dTMP) dTdT are added to the 3'-end of one RNA single strand having a length of 15-27 nucleotides designed according to the foregoing principles, and the other complementary RNA single strand is also treated in the same way, adding two deoxy-thymidine monophosphates (dTMP) dTdT to the 3'-end thereof. In this case, after the two complementary RNA single strands are annealed to form a double-stranded structure, each of the two ends of the double-stranded structure may form a 3' protruding end consisting of two deoxy-thymidine monophosphates (dTMP) dTdT respectively. In another embodiment of the present invention, two deoxy-thymidine monophosphates (dTMP) dTdT are added to the end of only one RNA single strand of a siRNA. In this case, after the two complementary RNA single strands are annealed to form a double-stranded structure, only one end of the double-stranded structure forms a 3' protruding end consisting of two deoxy-thymidine monophosphates (dTMP) dTdT.

One RNA single strand of the siRNA of the present invention may be synthesized by solid-phase or liquid-phase nucleic acid synthesis method. These methods comprise four process steps: 1) oligonucleotide synthesis; 2) deprotection; 3) purification and separation; and 4) desalination. The technical details of the four steps are well known to those skilled in the art, and thus will not be described in detail herein.

In addition to chemical synthesis, the siRNA of the present invention may also be obtained from expression of plasmid and/or virus vector. For example, design a DNA sequence with a length of 50-90 nucleotides, and add two different restriction enzyme cutting sites at its two ends, BamHI and EcoRI restriction sites for instance. The middle-segment sequence of the RNA transcript encoded by the designed DNA may form a loop structure, and the sequences at the two ends of the loop after the U-turn may form a complementarily paired double-stranded structure. By cloning technology, the designed DNA is inserted into an expression vector digested by the corresponding restriction enzyme. The expression vector is introduced into cells, and the RNA transcript generated from the designed DNA sequence may be processed into mature siRNA by cell's inherent siRNA processing mechanism. Thereby, siRNA may be expressed temporarily or stably in cells.

The chemical modification of the siRNA conducted by the present invention may be one chemical modification or a combination of more than one chemical modification selected from the following:

1) Modification of phosphodiester bond connecting nucleotide residues in the backbone structure of the RNA strands;
2) Modification of ribose in the backbone structure of the RNA strands;
3) Modification of base in the nucleotide residue of the RNA.

For example, the modification of phosphate group mentioned in the present invention refers to modification of oxygen in the phosphate group, including phosphorthioate modification and boranophosphate modification. As shown in the formulae below, the oxygen in the phosphate group is replaced by sulfur and borane, respectively. Both modifications can stabilize the structure of nucleic acid and maintain high specificity and high affinity of base pairing.

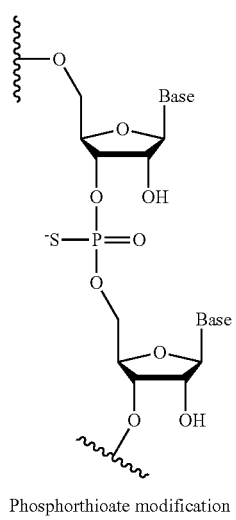

Phosphorthioate modification

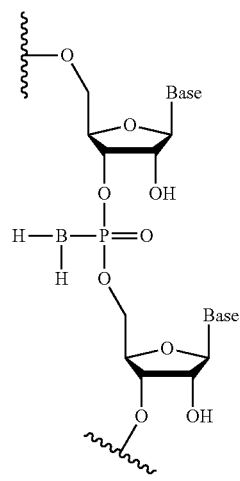

Boranophosphate modication

In the present invention, the modification of ribose group refers to modification of 2'-hydroxy (2'-OH) in the ribose group. Upon introducing certain substituents such as methoxy or fluoro at 2'-hydroxy position of the ribose group, ribonuclease in serum cannot easily digest nucleic acid, thereby improving the stability of the nucleic acid and allowing the nucleic acid to have stronger resistance against nuclease hydrolysis. The modification of 2'-hydroxy in the pentose of the nucleotide includes 2'-fluoro modification, 2'-methoxy modification, 2'-methoxyethoxy modification, 2'-2,4-dinitrophenol modification (2'-DNP modification), locked nucleic acid modification (LNA modification), 2'-amino modification, 2'-deoxy modification, etc.

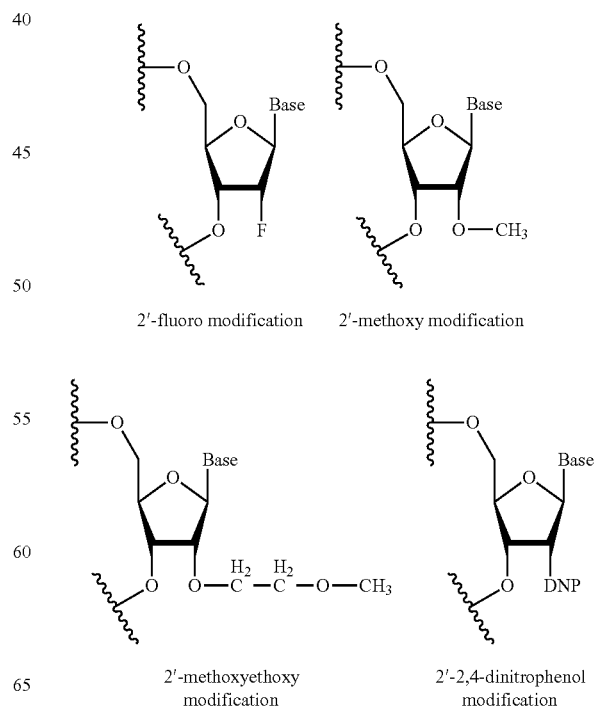

2'-fluoro modification         2'-methoxy modification

2'-methoxyethoxy modification         2'-2,4-dinitrophenol modification

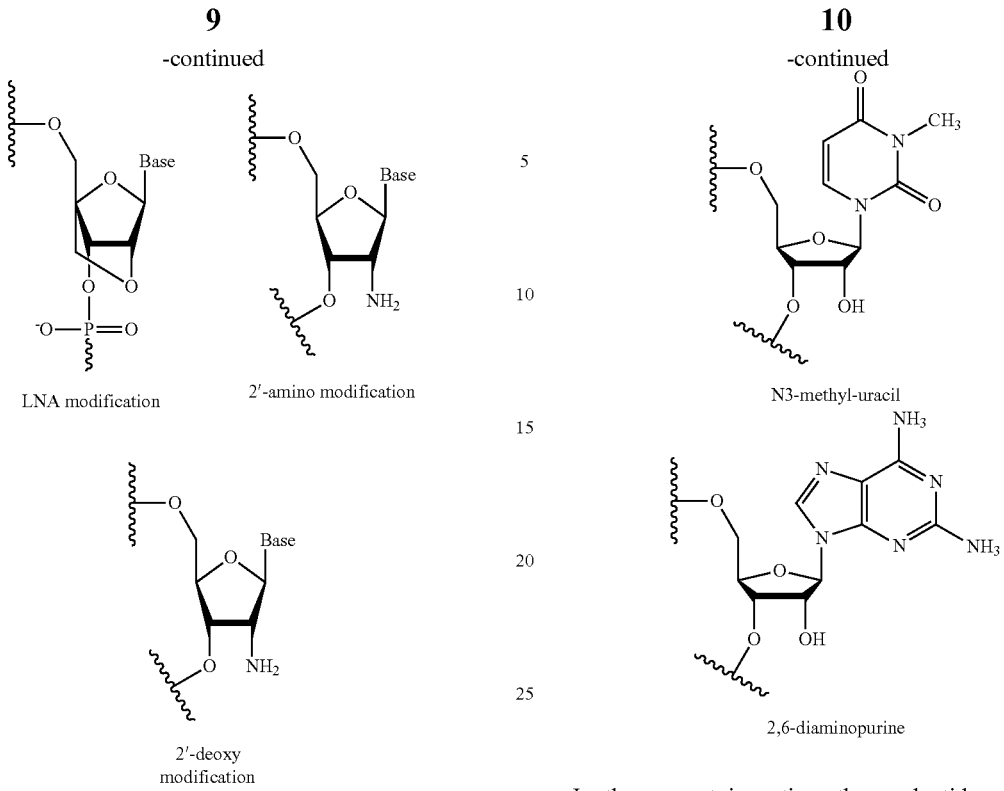

LNA modification

2'-amino modification

2'-deoxy modification

N3-methyl-uracil 2,6-diaminopurine

In the present invention, the modification of base refers to modification of the base in the nucleotide group. For example, 5'-bromo-uracil modification and 5'-iodo-uracil modification with bromine or iodine being introduced at 5-position of uracil are common modification methods for base. Modifications such as N3-methyl-uracil modification, 2,6-diaminopurine modification are also available.

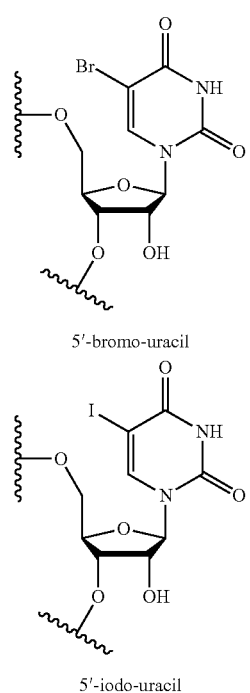

5'-bromo-uracil

5'-iodo-uracil

In the present invention, the nucleotide group with a modified ribose group is preferably a nucleotide group in which the 2'-hydroxy of the ribose group is substituted by methoxy or fluorine. Modified siRNAs have stronger resistance against nuclease enzymolysis, while their activity of inhibiting the expression of plk1 gene will not be obviously changed due to the modification.

In one embodiment of the present invention, in order to promote lipid solubility of siRNA, lipophilic groups such as cholesterol, lipoprotein, vitamin E and aliphatic chain may be introduced at the 5'-end or 3'-end of the sense strand of the siRNA. These lipophilic groups may bind to siRNA via covalent bond. Alternatively, the lipophilic groups may also bind to siRNA via non-covalent bond. For example, siRNA binds to a neutral phospholipid molecule, polypeptide, polysaccharide and the like via hydrophobic bond or ionic bond. It is known that the introduction of lipophilic groups to siRNA via covalent binding or non-covalent binding may improve the in vivo stability, blood metabolic performance and bioactivity of siRNA. In one embodiment of the present invention, the 5'-end and/or 3'-end of the first single strand (or sense strand) of the siRNA are attached with a 5'-cap and/or 3'-cap. The 5'-cap and/or 3'-cap structures may help siRNA resist the attack of exonuclease and thereby improve the in vivo stability of siRNA. The 5'-cap and/or 3'-cap may include, but is not limited to glycerol, inverted deoxy abasic isonucleoside (inverted deoxy abasic moiety), 4',5'-methylene nucleotide and the like. In one embodiment of the present invention, the 5'-end of the second single strand (or antisense strand) of the siRNA is attached with a phosphate group. It is known that the phosphate group at the 5'-end of the antisense strand of a siRNA may improve the activity of the siRNA.

In the present invention, the siRNA which inhibits the expression of plk1 gene may form a pharmaceutical composition with a vector system which assists in the in vivo delivery of drugs, and be applied in mammalian bodies in a form of a pharmaceutical composition. The vector system includes, but is not limited to a cationic ingredient, a non-cationic ingredient and a pharmaceutically acceptable carrier. In the present invention, the cationic ingredient may be, but is not limited to positively charged polypeptide or protein, cationic lipid, positively charged polymer, and the like. The positively charged polypeptide or protein may be for example, oligomeric arginine, oligomeric lysine, protamine and the like. The cationic lipid may be at least one of the cationic lipids selected from dimethyl di(octadecyl) ammonium bromide (DDAB), 1,2-dimyristoyl-3-trimethyl-ammonium propane, 1,2-dioleoyl-3-trimethylammonium propane (DOTAP), 1,2-dioleoyl-3-trimethylammonium propane methylsulfate, 1,2-dipalmitoyl-3-trimethylammonium propane, 1,2-distearyl-3-trimethylammonium propane, N-(1-(2,3-dioleyloxy)propyl)-N,N,N-trimethylammonium chloride (DOTMA), dimyristoyl-oxo-propyl-dimethyl-hydroxyethyl ammonium bromide (DMRIE), (1,2-dioleyloxy-propyl)-3-dimethyl-hydroxyethyl ammonium bromide (DO-RIE), dimethyl didodecyl ammonium bromide, N-(a-trimethyl-ammonium acetyl)-didodecyl-D-glutamine hydrochloride, N-(a-trimethyl-ammonium acetyl)-O,O'-bis-(1H,1H,2H,2H-perfluoro-decyl)-L-glutamine hydrochloride, O,O'-dilauroyl-N-(a-trimethyl-ammonium acetyl)diethanolamine hydrochloride, methylallyl didodecyl ammonium bromide, N-{p-(w-trimethyl-ammonium-butyl-oxo)-benzoyl}-didodecyl-L-glutamine hydrochloride, 9-(w-trimethyl-ammonium-butyl)-3,6-dilauroyl carbazole bromide, dimethyl-dioctadecyl ammonium hydrochloride, N-w-trimethyl-ammonium-decanoyl-dihexadecyl-D-glutamine bromide, N-{p-(w-trimethyl-ammonium-hexyl-oxo)-benzoyl}-dimyristyl)-L-glutamine bromide, p-(w-trimethyl-ammonium-decyl-oxo)-p'-octyloxy-azobenzene bromide salt (MC-1-0810), p-{w-(b-hydroxy-ethyl)dimethyl-ammonium-decyl-oxo}-p'-octyloxy-azobenzene bromide salt (MC-3-0810), O,O',O"-tris(lauroyl)-N-(w-trimethyl-ammonium decanoyl)-tris(hydroxyl-methyl) aminomethane bromide salt (TC-1-12), 1,2-dilauryl-glycero-3-ethylphosphocholine, 1,2-dimyristoyl-glycero-3-ethylphosphocholine, 1,2-dipalmitoyl-glycero-3-ethylphosphocholine, 1,2-distearoyl-glycero-3-ethylphosphocholine, 1,2-dioleoyl-glycero-3-ethylphosphocholine, 1-palmitoyl-2-oleoyl-glycero-3-ethylphosphocholine, N,N-dihydroxyethyl-N-methyl-N-2-(cholesteryloxycarbonylamino) ethylammonium bromide (BHEM-Chol), (2,3-dioleoyloxy) propyl-trimethylammonium chloride (DOTAP) and N-(1-(2, 3-dioleoyloxy)propyl)-N,N,N-trimethylammonium chloride. The positively charged polymer may be at least one of the positively charged polymers selected from polyethylenimine, poly β-amino ester and chitosan quaternary ammonium salt. In the present invention, the preferred cationic ingredient is N,N-dihydroxyethyl-N-methyl-N-2-(cholesteryloxycarbonylamino) ethylammonium bromide, (2,3-dioleoyloxypropyl) trimethylammonium chloride, N-(1-(2,3-dioleoyloxy)propyl)-N,N,N-trimethylammonium chloride, or poly β-amino ester of polycaprolactone-poly(N,N-dimethylaminoethylmethacrylate) block copolymer type.

In the pharmaceutical composition described in the present invention, the non-cationic ingredient may be, but is not limited to neutral fusogenic lipid, anionic lipid, amphiphilic polymer and the like. The fusogenic lipid may be for example, dioleoyl phosphatidylethanolamine, dioleoyl phosphatidylcholine, trans phosphatidylethanolamine, 1,2-bis(10,12-tricosane-diacyl)-ethanolamine phosphate, 1,2-bis-rac-oleoyl ethanolamine phosphate, 1,2-dihexadecyl ethanolamine phosphate, 1,2-dicaproyl ethanolamine phosphate, 1,2-dilauroyl ethanolamine phosphate, 1,2-dilinoleoyl ethanolamine phosphate, 1,2-dimyristoyl ethanolamine phosphate, 1,2-dioleoyl ethanolamine phosphate, 1,2-dipalmitoleoyl ethanolamine phosphate, 1,2-dipalmitoyl ethanolamine phosphate, 1,2-diphytanoyl ethanolamine phosphate, 1,2-distearoyl ethanolamine phosphate, 1-palmitoyl-2-oleoyl ethanolamine phosphate, 1-palmitoyl-2-(10, 12-tricosane-diacyl) ethanolamine phosphate, 1,2-dioleoyl ethanolamine phosphate-N-hexanamide, 1,2-dipalmitoyl ethanolamine phosphate-N-hexanamide, N,N-dimethyl-1,2-dioleoyl ethanolamine phosphate, N,N-dimethyl-1,2-dipalmitoyl ethanolamine phosphate, N-lauroyl-1,2-dipalmitoyl ethanolamine phosphate, N-lauroyl-1,2-dioleoyl ethanolamine phosphate, 1,2-dioleoyl ethanolamine phosphate-N-dodecyl amine, 1,2-dipalmitoyl ethanolamine phosphate-N-dodecyl amine, 1,2-dioleoyl ethanolamine phosphate-N-glutaryl, 1,2-dipalmitoyl ethanolamine phosphate-N-glutaryl, 1,2-dioleoyl ethanolamine phosphate-N-lactose, 1,2-dioleoyl ethanolamine phosphate-N-[4(p-maleimide-methyl)cyclohexanyl-carboxylate], dipalmitoyl ethanolamine phosphate-N-[4-(p-maleimide-methyl)cyclohexanyl-carboxylate], 1,2-dipalmitoyl ethanolamine phosphate-N-[4-(p-maleimide phenyl) butyramide], 1,2-dioleoyl ethanolamine phosphate-N-[4-(p-maleimide phenyObutyrate], N-methyl-1,2-dioleoyl ethanolamine phosphate, N-methyl-dipalmitoyl ethanolamine phosphate, 1,2-dioleoyl ethanolamine phosphate-N-[3-(2-pyridyldithio) propionate, 1,2-dipalmitoyl ethanolamine phosphate-N-[3-(2-pyridyldithio) propionate], N-(succinyl)-1,2-dioleoyl ethanolamine phosphate, N-(succinyl)-1,2-dipalmitoyl ethanolamine phosphate and the like. For the pharmaceutical composition of the present invention, by containing the foregoing fusogenic lipids, the transport and delivery efficiencies of the pharmaceutical composition in mammalian bodies can be further increased. The amphiphilic polymer may be for example, polyethylene glycol-polylactic acid diblock copolymer, polyethylene glycol-polylactic acid triblock copolymer, polyethylene glycol-poly(lactic acid-glycolic acid) diblock copolymer, or polyethylene glycol-poly(lactic acid-glycolic acid) triblock copolymer, polycaprolactone-polyphosphoester diblock copolymer, polycaprolactone-polyphosphoester triblock copolymer, polyethylene glycol-polycaprolactone diblock copolymer, polyethylene glycol-polycaprolactone triblock copolymer, wherein in the pharmaceutical composition of the present invention, dioleoyl phosphatidylethanolamine, or polyethylene glycol-polylactic acid block copolymer are preferably to be used as the non-cationic ingredient.

In the pharmaceutical composition of the present invention, the pharmaceutically acceptable carrier may be phosphate buffer solution (PBS) with a pH of 4.0-9.0, tris (hydroxymethyl) aminomethane hydrochloride buffer solution with a pH of 7.5-8.5, normal saline, or 7-15% sucrose solution, wherein phosphate buffer solution (PBS) with a pH of 4.0-9.0 is preferred to be used as the pharmaceutically acceptable carrier of the present invention. The pharmaceutical composition of the present invention may also contain a protective agent and/or an osmotic pressure regulator. The protective agent is one or more selected from inositol, sorbitol and sucrose. The osmotic pressure regulator may be sodium chloride and/or potassium chloride. Taking pharmaceutical compositions in a form of liquid preparation for injection for example, the content of the protective agent may be 0.01-30 wt %. There is no particular limitation to the content of the osmotic pressure regulator, as long as it can maintain the osmotic pressure of the liquid preparation at 200-700 milliosmol/kg. When the pharmaceutical composition of the present invention in the form of liquid preparation is applied to animal or human individuals, its dosage may be a dosage commonly used in the art.

For example, the dose for a single injection may be in the range of 1-10 g/kg body weight. During actual use, the dosage selection may be determined based on various parameters, particularly based on the age, body weight and symptoms of the animal or human individuals to be treated.

In the present invention, the pharmaceutical composition with the siRNA as an active ingredient may also contain an auxiliary ingredient which may enhance the stability of the pharmaceutical composition, maintain and enhance the inhibitory effect of the siRNA, and promote the metabolic performance and tissue targeting property of the pharmaceutical composition. The auxiliary ingredient may be, but is not limited to one or more selected from cholesterol, polypeptide, protein, polysaccharide, aliphatic chain, neutral phospholipid, and polyethylene glycol-lipid (PEG-lipid). There is no particular limitation to the content of the auxiliary ingredient in the pharmaceutical composition of the present invention, as long as it can enhance the stability, blood metabolic performance and target delivery effect of the pharmaceutical composition.

The method provided according to the present invention for inhibiting the expression of plk1 gene in mammalian cells comprises introducing the abovementioned siRNA which inhibits the expression of plk1 gene into mammalian cells, thereby allowing the introduced siRNA to sequence-specifically induce inhibition of the expression of plk1 gene.

In the present invention, when introducing siRNA into cells in vitro, a known method may be adopted. Common methods for introducing siRNA in vitro include electroporation method, microinjection method, calcium phosphate method, DEAE-dextran method, virus encapsulating method and liposome encapsulating method, wherein liposome encapsulating method has become a conventional in vitro introducing method for siRNA. In the present invention, as the liposome, commercial cationic liposome such as Lipofectamine 2000 (made by Invitrogen), Oligofectamine (made by Invitrogen) and Tfx50 (made by Promega) may be used. There is no particular limitation to the mixing ratio of the siRNA and the cationic liposome, as long as introduction can be effectively performed and no dose toxicity is exerted to the cells. For example, relative to 100 parts by weight of siRNA, the content of the cationic liposome may be 100-10000000 parts by weight. In the present invention, there are two methods for introducing siRNA into the cells in mammalian bodies. The first method is to directly introduce naked siRNA to easily accessible cells of skin tissue, ocular tissue, lung tissue and the like; and the second method is to systemically delivery siRNA in the form of the pharmaceutical composition of the present invention.

EXAMPLES

The present invention will be illustrated in conjunction with the Examples hereinafter. Unless otherwise specified, the reagents, culture media and other experimental materials used in the present invention are all commercial products.

Example 1

Design and Synthesis of siRNA

Against the mRNA sequence of human plk1 (Genbank accession number: NM_005030.3, SEQ ID NO: 1), according to the foregoing design principles, 132 siRNAs were obtained. The sequences of the obtained siRNAs are shown in Table 1, wherein 127 siRNAs (PLK-1~PLK-127) are distributed in the coding region of plk1 gene and the last 5 siRNAs (PLK-128~PLK-132) are distributed in the 3' untranslated region of plk1 gene. In Table 1, the sequences of the sense strand and the complementary antisense strand of each siRNA are listed, respectively. To be specific, for example, the sense strand of siRNA PLK-1 has a sequence represented by SEQ ID NO: 2 which is the same as the corresponding target site sequence in the plk1 mRNA sequence; and the antisense strand has a sequence represented by SEQ ID NO: 134 which is complementary to the corresponding target site sequence in the plk1 mRNA sequence. The sequences of the two single strands of each of the other siRNAs are numbered successively in the same way as applied to siRNA PLK-1.

TABLE 1 siRNA sequences against human mRNA

| No. | SEQ ID No. | Nucleotide sequence (5'→3') | Corresponding target site sequence in human mRNA (NM_005030.3) |
|---|---|---|---|
| PLK-1 | 2 | GCUCCACCGGCGAAAGAGA | 153-171 |
|  | 134 | UCUCUUUCGCCGGUGGAGC |  |
| PLK-2 | 3 | CCAAGUGCUUCGAGAUCUC | 247-265 |
|  | 135 | GAGAUCUCGAAGCACUUGG |  |
| PLK-3 | 4 | GUGCUUCGAGAUCUCGGAC | 251-269 |
|  | 136 | GUCCGAGAUCUCGAAGCAC |  |
| PLK-4 | 5 | UCUCGGACGCGGACACCAA | 262-280 |
|  | 137 | UUGGUGUCCGCGUCCGAGA |  |
| PLK-5 | 6 | CAAGAUUGUGCCUAAGUCU | 296-314 |
|  | 138 | AGACUUAGGCACAAUCUUG |  |
| PLK-6 | 7 | GAUUGUGCCUAAGUCUCUG | 299-317 |
|  | 139 | CAGAGACUUAGGCACAAUC |  |
| PLK-7 | 8 | CUAAGUCUCUGCUGCUCAA | 307-325 |
|  | 140 | UUGAGCAGCAGAGACUUAG |  |
| PLK-8 | 9 | AAGCCGCACCAGAGGGAGA | 324-342 |
|  | 141 | UCUCCCUCUGGUGCGGCUU |  |
| PLK-9 | 10 | GAUGUCCAUGGAAAUAUCC | 344-362 |
|  | 142 | GGAUAUUUCCAUGGACAUC |  |
| PLK-10 | 11 | AUGGAAAUAUCCAUUCACC | 351-369 |
|  | 143 | GGUGAAUGGAUAUUUCCAU |  |
| PLK-11 | 12 | GAAAUAUCCAUUCACCGCA | 354-372 |
|  | 144 | UGCGGUGAAUGGAUAUUUC |  |
| PLK-12 | 13 | AUAUCCAUUCACCGCAGCC | 357-375 |
|  | 145 | GGCUGCGGUGAAUGGAUAU |  |
| PLK-13 | 14 | ACCAGCACGUCGUAGGAUU | 382-400 |
|  | 146 | AAUCCUACGACGUGCUGGU |  |
| PLK-14 | 15 | UCGUAGGAUUCCACGGCUU | 391-409 |
|  | 147 | AAGCCGUGGAAUCCUACGA |  |
| PLK-15 | 16 | CGUAGGAUUCCACGGCUUU | 392-410 |
|  | 148 | AAAGCCGUGGAAUCCUACG |  |
| PLK-16 | 17 | CGACUUCGUGUUCGUGGUG | 422-440 |
|  | 149 | CACCACGAACACGAAGUCG |  |
| PLK-17 | 18 | ACUUCGUGUUCGUGGUGUU | 424-442 |
|  | 150 | AACACCACGAACACGAAGU |  |
| PLK-18 | 19 | GCUGCACAAGAGGAGGAAA | 473-491 |
|  | 151 | UUUCCUCCUCUUGUGCAGC |  |

TABLE 1-continued siRNA sequences against human mRNA

| No. | SEQ ID No. | Nucleotide sequence (5'→3') | Corresponding target site sequence in human mRNA (NM_005030.3) |
|---|---|---|---|
| PLK-19 | 20<br>152 | CUGCACAAGAGGAGGAAAG<br>CUUUCCUCCUCUUGUGCAG | 474-492 |
| PLK-20 | 21<br>153 | GGAGGAAAGCCCUGACUGA<br>UCAGUCAGGGCUUUCCUCC | 484-502 |
| PLK-21 | 22<br>154 | CCGAUACUACCUACGGCAA<br>UUGCCGUAGGUAGUAUCGG | 512-530 |
| PLK-22 | 23<br>155 | CGAUACUACCUACGGCAAA<br>UUUGCCGUAGGUAGUAUCG | 513-531 |
| PLK-23 | 24<br>156 | GAUACUACCUACGGCAAAU<br>AUUUGCCGUAGGUAGUAUC | 514-532 |
| PLK-24 | 25<br>157 | CCUACGGCAAAUUGUGCUU<br>AAGCACAAUUUGCCGUAGG | 521-539 |
| PLK-25 | 26<br>158 | AUUGUGCUUGGCUGCCAGU<br>ACUGGCAGCCAAGCACAAU | 531-549 |
| PLK-26 | 27<br>159 | GCCAGUACCUGCACCGAAA<br>UUUCGGUGCAGGUACUGGC | 544-562 |
| PLK-27 | 28<br>160 | CUGCACCGAAACCGAGUUA<br>UAACUCGGUUUCGGUGCAG | 552-570 |
| PLK-28 | 29<br>161 | GCACCGAAACCGAGUUAUU<br>AAUAACUCGGUUUCGGUGC | 554-572 |
| PLK-29 | 30<br>162 | CCGAAACCGAGUUAUUCAU<br>AUGAAUAACUCGGUUUCGG | 557-575 |
| PLK-30 | 31<br>163 | AAACCGAGUUAUUCAUCGA<br>UCGAUGAAUAACUCGGUUU | 560-578 |
| PLK-31 | 32<br>164 | ACCGAGUUAUUCAUCGAGA<br>UCUCGAUGAAUAACUCGGU | 562-580 |
| PLK-32 | 33<br>165 | AGUUAUUCAUCGAGACCUC<br>GAGGUCUCGAUGAAUAACU | 566-584 |
| PLK-33 | 34<br>166 | GAGACCUCAAGCUGGGCAA<br>UUGCCCAGCUUGAGGUCUC | 577-595 |
| PLK-34 | 35<br>167 | UGAUGAAGAUCUGGAGGU<br>ACCUCCAGAUCUUCAUUCA | 604-622 |
| PLK-35 | 36<br>168 | GAAUGAAGAUCUGGAGGUG<br>CACCUCCAGAUCUUCAUUC | 605-623 |
| PLK-36 | 37<br>169 | AUGAAGAUCUGGAGGUGAA<br>UUCACCUCCAGAUCUUCAU | 607-625 |
| PLK-37 | 38<br>170 | UGAAGAUCUGGAGGUGAAA<br>UUUCACCUCCAGAUCUUCA | 608-626 |
| PLK-38 | 39<br>171 | GGCAACCAAAGUCGAAUAU<br>AUAUUCGACUUUGGUUGCC | 644-662 |
| PLK-39 | 40<br>172 | CAACCAAAGUCGAAUAUGA<br>UCAUAUUCGACUUUGGUUG | 646-664 |
| PLK-40 | 41<br>173 | ACCAAAGUCGAAUAUGACG<br>CGUCAUAUUCGACUUUGGU | 648-666 |
| PLK-41 | 42<br>174 | CCAAAGUCGAAUAUGACGG<br>CCGUCAUAUUCGACUUUGG | 649-667 |
| PLK-42 | 43<br>175 | AGUCGAAUAUGACGGGGAG<br>CUCCCCGUCAUAUUCGACU | 653-671 |
| PLK-43 | 44<br>176 | UAUGACGGGGAGAGGAAGA<br>UCUUCCUCUCCCCGUCAUA | 660-678 |
| PLK-44 | 45<br>177 | CUGUGUGGGACUCCUAAUU<br>AAUUAGGAGUCCCACACAG | 684-702 |
| PLK-45 | 46<br>178 | GUGGGACUCCUAAUUACAU<br>AUGUAAUUAGGAGUCCCAC | 688-706 |
| PLK-46 | 47<br>179 | UGGGACUCCUAAUUACAUA<br>UAUGUAAUUAGGAGUCCCA | 689-707 |
| PLK-47 | 48<br>180 | GACUCCUAAUUACAUAGCU<br>AGCUAUGUAAUUAGGAGUC | 692-710 |
| PLK-48 | 49<br>181 | CUAAUUACAUAGCUCCCGA<br>UCGGGAGCUAUGUAAUUAG | 697-715 |
| PLK-49 | 50<br>182 | UUACAUAGCUCCCGAGGUG<br>CACCUCGGGAGCUAUGUAA | 701-719 |
| PLK-50 | 51<br>183 | GCAAGAAGGGCACAGUUUU<br>AAACUGUGCCCUUCUUGC | 724-742 |
| PLK-51 | 52<br>184 | GAAAGGGCACAGUUUCGAG<br>CUCGAAACUGUGCCCUUUC | 728-746 |
| PLK-52 | 53<br>185 | CCAUUGGGUGUAUCAUGUA<br>UACAUGAUACACCCAAUGG | 760-778 |
| PLK-53 | 54<br>186 | CAUUGGGUGUAUCAUGUAU<br>AUACAUGAUACACCCAAUG | 761-779 |
| PLK-54 | 55<br>187 | GGUGUAUCAUGUAUACCUU<br>AAGGUAUACAUGAUACACC | 766-784 |
| PLK-55 | 56<br>188 | AUCAUGUAUACCUUGUUAG<br>CUAACAAGGUAUACAUGAU | 771-789 |
| PLK-56 | 57<br>189 | AUGUAUACCUUGUUAGUGG<br>CCACUAACAAGGUAUACAU | 774-792 |
| PLK-57 | 58<br>190 | AUACCUUGUUAGUGGGCAA<br>UUGCCCACUAACAAGGUAU | 778-796 |
| PLK-58 | 59<br>191 | CUUGUUAGUGGGCAAACCA<br>UGGUUUGCCCACUAACAAG | 782-800 |
| PLK-59 | 60<br>192 | UUUGAGACUUCUUGCCUAA<br>UUAGGCAAGAAGUCUCAAA | 804-822 |
| PLK-60 | 61<br>193 | AGAGACCUACCUCCGGAUC<br>GAUCCGGAGGUAGGUCUCU | 824-842 |
| PLK-61 | 62<br>194 | GAGACCUACCUCCGGAUCA<br>UGAUCCGGAGGUAGGUCUC | 825-843 |
| PLK-62 | 63<br>195 | CCUCCGGAUCAAGAAGAAU<br>AUUCUUCUUGAUCCGGAGG | 833-851 |
| PLK-63 | 64<br>196 | CCGGAUCAAGAAGAAUGAA<br>UUCAUUCUUCUUGAUCCGG | 836-854 |
| PLK-64 | 65<br>197 | CGGAUCAAGAAGAAUGAAU<br>AUUCAUUCUUCUUGAUCCG | 837-855 |
| PLK-65 | 66<br>198 | GGAUCAAGAAGAAUGAAUA<br>UAUUCAUUCUUCUUGAUCC | 838-856 |
| PLK-66 | 67<br>199 | GAUCAAGAAGAAUGAAUAC<br>GUAUUCAUUCUUCUUGAUC | 839-857 |

TABLE 1-continued siRNA sequences against human mRNA

| No. | SEQ ID No. | Nucleotide sequence (5'→3') | Corresponding target site sequence in human mRNA (NM_005030.3) |
|---|---|---|---|
| PLK-67 | 68<br>200 | CAAGAAGAAUGAAUACAGU<br>ACUGUAUUCAUUCUUCUUG | 842-860 |
| PLK-68 | 69<br>201 | GAAGAAUGAAUACAGUAUU<br>AAUACUGUAUUCAUUCUUC | 845-863 |
| PLK-69 | 70<br>202 | GAAUGAAUACAGUAUUCCC<br>GGGAAUACUGUAUUCAUUC | 848-866 |
| PLK-70 | 71<br>203 | UGAAUACAGUAUUCCCAAG<br>CUUGGGAAUACUGUAUUCA | 851-869 |
| PLK-71 | 72<br>204 | UACAGUAUUCCCAAGCACA<br>UGUGCUUGGGAAUACUGUA | 855-873 |
| PLK-72 | 73<br>205 | GUAUUCCCAAGCACAUCAA<br>UUGAUGUGCUUGGGAAUAC | 859-877 |
| PLK-73 | 74<br>206 | GAUGCUUCAGACAGAUCCC<br>GGGAUCUGUCUGAAGCAUC | 905-923 |
| PLK-74 | 75<br>207 | CAACCAUUAACGAGCUGCU<br>AGCAGCUCGUUAAUGGUUG | 934-952 |
| PLK-75 | 76<br>208 | CCAUUAACGAGCUGCUUAA<br>UUAAGCAGCUCGUUAAUGG | 937-955 |
| PLK-76 | 77<br>209 | CGAGCUGCUUAAUGACGAG<br>CUCGUCAUUAAGCAGCUCG | 944-962 |
| PLK-77 | 78<br>210 | GCUUAAUGACGAGUUCUUU<br>AAAGAACUCGUCAUUAAGC | 950-968 |
| PLK-78 | 79<br>211 | CUUAAUGACGAGUUCUUUA<br>UAAAGAACUCGUCAUUAAG | 951-969 |
| PLK-79 | 80<br>212 | UGACGAGUUCUUUACUUCU<br>AGAAGUAAAGAACUCGUCA | 956-974 |
| PLK-80 | 81<br>213 | GAGUUCUUUACUUCUGGCU<br>AGCCAGAAGUAAAGAACUC | 960-978 |
| PLK-81 | 82<br>214 | GUUCUUUACUUCUGGCUAU<br>AUAGCCAGAAGUAAAGAAC | 962-980 |
| PLK-82 | 83<br>215 | CUUUACUUCUGGCUAUAUC<br>GAUAUAGCCAGAAGUAAAG | 965-983 |
| PLK-83 | 84<br>216 | GACCAUUCCACCAAGGUUU<br>AAACCUUGGUGGAAUGGUC | 1010-1028 |
| PLK-84 | 85<br>217 | CCCUCACAGUCCUCAAUAA<br>UUAUUGAGGACUGUGAGGG | 1069-1087 |
| PLK-85 | 86<br>218 | CCUCACAGUCCUCAAUAAA<br>UUUAUUGAGGACUGUGAGG | 1070-1088 |
| PLK-86 | 87<br>219 | CAGUCCUCAAUAAAGGCUU<br>AAGCCUUUAUUGAGGACUG | 1075-1093 |
| PLK-87 | 88<br>220 | CUCAAUAAAGGCUUGGAGA<br>UCUCCAAGCCUUUAUUGAG | 1080-1098 |
| PLK-88 | 89<br>221 | UCAAUAAAGGCUUGGAGAA<br>UUCUCCAAGCCUUUAUUGA | 1081-1099 |
| PLK-89 | 90<br>222 | CAAUAAAGGCUUGGAGAAC<br>GUUCUCCAAGCCUUUAUUG | 1082-1100 |
| PLK-90 | 91<br>223 | UAAAGGCUUGGAGAACCCC<br>GGGGUUCUCCAAGCCUUUA | 1085-1103 |
| PLK-91 | 92<br>224 | AGAAGAACCAGUGGUUCGA<br>UCGAACCACUGGUUCUUCU | 1127-1145 |
| PLK-92 | 93<br>225 | GAACCAGUGGUUCGAGAGA<br>UCUCUCGAACCACUGGUUC | 1131-1149 |
| PLK-93 | 94<br>226 | CCAGUGGUUCGAGAGACAG<br>CUGUCUCUCGAACCACUGG | 1134-1152 |
| PLK-94 | 95<br>227 | AGACAGGUGAGGUGGUCGA<br>UCGACCACCUCACCUGUCU | 1147-1165 |
| PLK-95 | 96<br>228 | GGCAAGAGGAGGCUGAGGA<br>UCCUCAGCCUCCUCUUGCC | 1240-1258 |
| PLK-96 | 97<br>229 | GCAAGAGGAGGCUGAGGAU<br>AUCCUCAGCCUCCUCUUGC | 1241-1259 |
| PLK-97 | 98<br>230 | AAGAGGAGGCUGAGGAUCC<br>GGAUCCUCAGCCUCCUCUU | 1243-1261 |
| PLK-98 | 99<br>231 | CCAUCUUCUGGGUCAGCAA<br>UUGCUGACCCAGAAGAUGG | 1273-1291 |
| PLK-99 | 100<br>232 | UCAGCAAGUGGGUGGACUA<br>UAGUCCACCCACUUGCUGA | 1285-1303 |
| PLK-100 | 101<br>233 | CAGCAAGUGGGUGGACUAU<br>AUAGUCCACCCACUUGCUG | 1286-1304 |
| PLK-101 | 102<br>234 | GCAAGUGGGUGGACUAUUC<br>GAAUAGUCCACCCACUUGC | 1288-1306 |
| PLK-102 | 103<br>235 | GGACUAUUCGGACAAGUAC<br>GUACUUGUCCGAAUAGUCC | 1298-1316 |
| PLK-103 | 104<br>236 | GGUAUCAGCUCUGUGAUAA<br>UUAUCACAGAGCUGAUACC | 1324-1342 |
| PLK-104 | 105<br>237 | GGUGCUCUUCAAUGACUCA<br>UGAGUCAUUGAAGAGCACC | 1352-1370 |
| PLK-105 | 106<br>238 | GCUCUUCAAUGACUCAACA<br>UGUUGAGUCAUUGAAGAGC | 1355-1373 |
| PLK-106 | 107<br>239 | UGACUCAACACGCCUCAUC<br>GAUGAGGCGUGUUGAGUCA | 1364-1382 |
| PLK-107 | 108<br>240 | CACGCCUCAUCCUCUACAA<br>UUGUAGAGGAUGAGGCGUG | 1372-1390 |
| PLK-108 | 109<br>241 | CUACAAUGAUGGUGCAGC<br>GCUGUCACCAUCAUUGUAG | 1385-1403 |
| PLK-109 | 110<br>242 | GGUGACAGCUGCAGUACA<br>UGUACUGCAGGCUGUCACC | 1395-1413 |
| PLK-110 | 111<br>243 | GUGACAGCUGCAGUACAU<br>AUGUACUGCAGGCUGUCAC | 1396-1414 |
| PLK-111 | 112<br>244 | CCCAACUCCUUGAUGAAGA<br>UCUUCAUCAAGGAGUUGGG | 1458-1476 |
| PLK-112 | 113<br>245 | CCAACUCCUUGAUGAAGAA<br>UUCUUCAUCAAGGAGUUGG | 1459-1477 |
| PLK-113 | 114<br>246 | ACUCCUUGAUGAAGAAGAU<br>AUCUUCUUCAUCAAGGAGU | 1462-1480 |
| PLK-114 | 115<br>247 | CUCCUUGAUGAAGAAGAUC<br>GAUCUUCUUCAUCAAGGAG | 1463-1481 |

TABLE 1-continued siRNA sequences against human mRNA

| No. | SEQ ID No. | Nucleotide sequence (5'→3') | Corresponding target site sequence in human mRNA (NM_005030.3) |
|---|---|---|---|
| PLK-115 | 116<br>248 | GAAGAAGAUCACCCUCCUU<br>AAGGAGGGUGAUCUUCUUC | 1472-1490 |
| PLK-116 | 117<br>249 | GAAGAUCACCCUCCUUAAA<br>UUUAAGGAGGGUGAUCUUC | 1475-1493 |
| PLK-117 | 118<br>250 | GAUCACCCUCCUUAAAUAU<br>AUAUUUAAGGAGGGUGAUC | 1478-1496 |
| PLK-118 | 119<br>251 | AUAUUUCCGCAAUUACAUG<br>CAUGUAAUUGCGGAAAUAU | 1493-1511 |
| PLK-119 | 120<br>252 | UUACAUGAGCGAGCACUUG<br>CAAGUGCUCGCUCAUGUAA | 1505-1523 |
| PLK-120 | 121<br>253 | GCAGCGUGCAGAUCAACUU<br>AAGUUGAUCUGCACGCUGC | 1636-1654 |
| PLK-121 | 122<br>254 | GCGUGCAGAUCAACUUCUU<br>AAGAAGUUGAUCUGCACGC | 1639-1657 |
| PLK-122 | 123<br>255 | AGAUCAACUUCUUCCAGGA<br>UCCUGGAAGAAGUUGAUCU | 1645-1663 |
| PLK-123 | 124<br>256 | GAUCAACUUCUUCCAGGAU<br>AUCCUGGAAGAAGUUGAUC | 1646-1664 |
| PLK-124 | 125<br>257 | UCAACUUCUUCCAGGAUCA<br>UGAUCCUGGAAGAAGUUGA | 1648-1666 |
| PLK-125 | 126<br>258 | CUUCUUCCAGGAUCACACC<br>GGUGUGAUCCUGGAAGAAG | 1652-1670 |
| PLK-126 | 127<br>259 | GAUCACACCAAGCUCAUCU<br>AGAUGAGCUUGGUGUGAUC | 1662-1680 |
| PLK-127 | 128<br>260 | UGAUGGCAGCCGUGACCUA<br>UAGGUCACGGCUGCCAUCA | 1690-1708 |
| PLK-128 | 129<br>261 | GCAGAGCUGCAUCAUCCUU<br>AAGGAUGAUGCAGCUCUGC | 1982-2000 |
| PLK-129 | 130<br>262 | CCCACCAUAUGAAUUGUAC<br>GUACAAUUCAUAUGGUGGG | 2081-2099 |
| PLK-130 | 131<br>263 | CCACCAUAUGAAUUGUACA<br>UGUACAAUUCAUAUGGUGG | 2082-2100 |
| PLK-131 | 132<br>264 | CACCAUAUGAAUUGUACAG<br>CUGUACAAUUCAUAUGGUG | 2083-2101 |
| PLK-132 | 133<br>265 | UCCUUUCCUUGGCUUUAUG<br>CAUAAAGCCAAGGAAAGGA | 2127-2145 |

The foregoing 132 siRNAs were further analyzed according to species homology and 12 human-mouse homologous siRNA sequences were obtained. The result is shown in Table 2. Likewise, 11 human-rat homologous siRNA sequences, 105 human-macaque homologous siRNA sequences and 119 human-chimpanzee homologous siRNA sequences were obtained. These results are shown in Table 3 Table 5, respectively.

TABLE 2

Human-mouse homologous siRNA sequences

| No. | SEQ ID No. | Nucleotide sequence (5'→3') | Corresponding target site sequence in human mRNA (NM_005030.3) | Corresponding target site sequence in mouse mRNA (NM_011121.3) |
|---|---|---|---|---|
| PLK-60 | 61<br>193 | AGAGACCUACCUCCGGAUC<br>GAUCCGGAGGUAGGUCUCU | 824-842 | 877-895 |
| PLK-61 | 62<br>194 | GAGACCUACCUCCGGAUCA<br>UGAUCCGGAGGUAGGUCUC | 825-843 | 878-896 |
| PLK-70 | 71<br>203 | UGAAUACAGUAUUCCCAAG<br>CUUGGGAAUACUGUAUUCA | 851-869 | 904-922 |
| PLK-71 | 72<br>204 | UACAGUAUUCCCAAGCACA<br>UGUGCUUGGGAAUACUGUA | 855-873 | 908-926 |
| PLK-72 | 73<br>205 | GUAUUCCCAAGCACAUCAA<br>UUGAUGUGCUUGGGAAUAC | 859-877 | 912-930 |
| PLK-95 | 96<br>228 | GGCAAGAGGAGGCUGAGGA<br>UCCUCAGCCUCCUCUUGCC | 1240-1258 | 1293-1311 |
| PLK-96 | 97<br>229 | GCAAGAGGAGGCUGAGGAU<br>AUCCUCAGCCUCCUCUUGC | 1241-1259 | 1294-1312 |
| PLK-97 | 98<br>230 | AAGAGGAGGCUGAGGAUCC<br>GGAUCCUCAGCCUCCUCUU | 1243-1261 | 1296-1314 |
| PLK-98 | 99<br>231 | CCAUCUUCGGGGUCAGCAA<br>UUGCUGACCCCGAAGAUGG | 1273-1291 | 1326-1344 |
| PLK-99 | 100<br>232 | UCAGCAAGUGGGUGGACUA<br>UAGUCCACCCACUUGCUGA | 1285-1303 | 1338-1356 |

TABLE 2-continued

Human-mouse homologous siRNA sequences

| No. | SEQ ID No. | Nucleotide sequence (5'→3') | Corresponding target site sequence in human mRNA (NM_005030.3) | Corresponding target site sequence in mouse mRNA (NM_011121.3) |
|---|---|---|---|---|
| PLK-100 | 101<br>233 | CAGCAAGUGGGUGGACUAU<br>AUAGUCCACCCACUUGCUG | 1286-1304 | 1339-1357 |
| PLK-101 | 102<br>234 | GCAAGUGGGUGGACUAUUC<br>GAAUAGUCCACCCACUUGC | 1288-1306 | 1341-1359 |

TABLE 3

Human-rat homologous siRNA sequences

| No. | SEQ ID No. | Nucleotide sequence (5'→3') | Corresponding target site sequence in human mRNA (NM_005030.3) | Corresponding target site sequence in rat mRNA (NM_017100.1) |
|---|---|---|---|---|
| PLK-60 | 61<br>193 | AGAGACCUACCUCCGGAUC<br>GAUCCGGAGGUAGGUCUCU | 824-842 | 865-883 |
| PLK-61 | 62<br>194 | GAGACCUACCUCCGGAUCA<br>UGAUCCGGAGGUAGGUCUC | 825-843 | 866-884 |
| PLK-70 | 71<br>203 | UGAAUACAGUAUUCCCAAG<br>CUUGGGAAUACUGUAUUCA | 851-869 | 892-910 |
| PLK-71 | 72<br>204 | UACAGUAUUCCCAAGCACA<br>UGUGCUUGGGAAUACUGUA | 855-873 | 896-914 |
| PLK-72 | 73<br>205 | GUAUUCCCAAGCACAUCAA<br>UUGAUGUGCUUGGGAAUAC | 859-877 | 900-918 |
| PLK-106 | 107<br>239 | UGACUCAACACGCCUCAUC<br>GAUGAGGCGUGUUGAGUCA | 1364-1382 | 1405-1423 |
| PLK-107 | 108<br>240 | CACGCCUCAUCCUCUACAA<br>UUGUAGAGGAUGAGGCGUG | 1372-1390 | 1413-1431 |
| PLK-111 | 112<br>244 | CCCAACUCCUUGAUGAAGA<br>UCUUCAUCAAGGAGUUGGG | 1458-1476 | 1499-1517 |
| PLK-112 | 113<br>245 | CCAACUCCUUGAUGAAGAA<br>UUCUUCAUCAAGGAGUUGG | 1459-1477 | 1500-1518 |
| PLK-113 | 114<br>246 | ACUCCUUGAUGAAGAAGAU<br>AUCUUCUUCAUCAAGGAGU | 1462-1480 | 1503-1521 |
| PLK-114 | 115<br>247 | CUCCUUGAUGAAGAAGAUC<br>GAUCUUCUUCAUCAAGGAG | 1463-1481 | 1504-1522 |

TABLE 4

Human-macaque homologous siRNA sequences

| No. | SEQ ID No. | Nucleotide sequence (5'→3') | Corresponding target site sequence in human mRNA (NM_005030.3) | Corresponding target site sequence in macaque mRNA (XM_001092070.2) |
|---|---|---|---|---|
| PLK-1 | 2<br>134 | GCUCCACCGGCGAAAGAGA<br>UCUCUUUCGCCGGUGGAGC | 153-171 | 376-394 |
| PLK-2 | 3<br>135 | CCAAGUGCUUCGAGAUCUC<br>GAGAUCUCGAAGCACUUGG | 247-265 | 470-488 |
| PLK-3 | 4<br>136 | GUGCUUCGAGAUCUCGGAC<br>GUCCGAGAUCUCGAAGCAC | 251-269 | 474-492 |
| PLK-4 | 5<br>137 | UCUCGGACGCGGACACCAA<br>UUGGUGUCCGCGUCCGAGA | 262-280 | 485-503 |
| PLK-5 | 6<br>138 | CAAGAUUGUGCCUAAGUCU<br>AGACUUAGGCACAAUCUUG | 296-314 | 519-537 |

TABLE 4-continued

Human-macaque homologous siRNA sequences

| No. | SEQ ID No. | Nucleotide sequence (5'→3') | Corresponding target site sequence in human mRNA (NM_005030.3) | Corresponding target site sequence in macaque mRNA (XM_001092070.2) |
|---|---|---|---|---|
| PLK-6 | 7<br>139 | GAUUGUGCCUAAGUCUCUG<br>CAGAGACUUAGGCACAAUC | 299-317 | 522-540 |
| PLK-8 | 9<br>141 | AAGCCGCACCAGAGGGAGA<br>UCUCCCUCUGGUGCGGCUU | 324-342 | 547-565 |
| PLK-9 | 10<br>142 | GAUGUCCAUGGAAAUAUCC<br>GGAUAUUUCCAUGGACAUC | 344-362 | 567-585 |
| PLK-10 | 11<br>143 | AUGGAAAUAUCCAUUCACC<br>GGUGAAUGGAUAUUUCCAU | 351-369 | 574-592 |
| PLK-11 | 12<br>144 | GAAAUAUCCAUUCACCGCA<br>UGCGGUGAAUGGAUAUUUC | 354-372 | 577-595 |
| PLK-12 | 13<br>145 | AUAUCCAUUCACCGCAGCC<br>GGCUGCGGUGAAUGGAUAU | 357-375 | 580-598 |
| PLK-13 | 14<br>146 | ACCAGCACGUCGUAGGAUU<br>AAUCCUACGACGUGCUGGU | 382-400 | 605-623 |
| PLK-14 | 15<br>147 | UCGUAGGAUUCCACGGCUU<br>AAGCCGUGGAAUCCUACGA | 391-409 | 614-632 |
| PLK-15 | 16<br>148 | CGUAGGAUUCCACGGCUUU<br>AAAGCCGUGGAAUCCUACG | 392-410 | 615-633 |
| PLK-16 | 17<br>149 | CGACUUCGUGUUCGUGGUG<br>CACCACGAACACGAAGUCG | 422-440 | 645-663 |
| PLK-17 | 18<br>150 | ACUUCGUGUUCGUGGUGUU<br>AACACCACGAACACGAAGU | 424-442 | 647-665 |
| PLK-18 | 19<br>151 | GCUGCACAAGAGGAGGAAA<br>UUUCCUCCUCUUGUGCAGC | 473-491 | 696-714 |
| PLK-19 | 20<br>152 | CUGCACAAGAGGAGGAAAG<br>CUUUCCUCCUCUUGUGCAG | 474-492 | 697-715 |
| PLK-20 | 21<br>153 | GGAGGAAAGCCCUGACUGA<br>UCAGUCAGGGCUUUCCUCC | 484-502 | 707-725 |
| PLK-27 | 28<br>160 | CUGCACCGAAACCGAGUUA<br>UAACUCGGUUUCGGUGCAG | 552-570 | 775-793 |
| PLK-28 | 29<br>161 | GCACCGAAACCGAGUUAUU<br>AAUAACUCGGUUUCGGUGC | 554-572 | 777-795 |
| PLK-33 | 34<br>166 | GAGACCUCAAGCUGGGCAA<br>UUGCCCAGCUUGAGGUCUC | 577-595 | 800-818 |
| PLK-34 | 35<br>167 | UGAAUGAAGAUCUGGAGGU<br>ACCUCCAGAUCUUCAUUCA | 604-622 | 827-845 |
| PLK-35 | 36<br>168 | GAAUGAAGAUCUGGAGGUG<br>CACCUCCAGAUCUUCAUUC | 605-623 | 828-846 |
| PLK-36 | 37<br>169 | AUGAAGAUCUGGAGGUGAA<br>UUCACCUCCAGAUCUUCAU | 607-625 | 830-848 |
| PLK-37 | 38<br>170 | UGAAGAUCUGGAGGUGAAA<br>UUUCACCUCCAGAUCUUCA | 608-626 | 831-849 |
| PLK-38 | 39<br>171 | GGCAACCAAAGUCGAAUAU<br>AUAUUCGACUUUGGUUGCC | 644-662 | 867-885 |
| PLK-39 | 40<br>172 | CAACCAAAGUCGAAUAUGA<br>UCAUAUUCGACUUUGGUUG | 646-664 | 869-887 |
| PLK-40 | 41<br>173 | ACCAAAGUCGAAUAUGACG<br>CGUCAUAUUCGACUUUGGU | 648-666 | 871-889 |
| PLK-41 | 42<br>174 | CCAAAGUCGAAUAUGACGG<br>CCGUCAUAUUCGACUUUGG | 649-667 | 872-890 |

TABLE 4-continued

Human-macaque homologous siRNA sequences

| No. | SEQ ID No. | Nucleotide sequence (5'→3') | Corresponding target site sequence in human mRNA (NM_005030.3) | Corresponding target site sequence in macaque mRNA (XM_001092070.2) |
|---|---|---|---|---|
| PLK-42 | 43 175 | AGUCGAAUAUGACGGGAG CUCCCCGUCAUAUUCGACU | 653-671 | 876-894 |
| PLK-43 | 44 176 | UAUGACGGGAGAGGAAGA UCUUCCUCUCCCCGUCAUA | 660-678 | 883-901 |
| PLK-47 | 48 180 | GACUCCUAAUUACAUAGCU AGCUAUGUAAUUAGGAGUC | 692-710 | 915-933 |
| PLK-48 | 49 181 | CUAAUUACAUAGCUCCCGA UCGGGAGCUAUGUAAUUAG | 697-715 | 920-938 |
| PLK-49 | 50 182 | UUACAUAGCUCCCGAGGUG CACCUCGGGAGCUAUGUAA | 701-719 | 924-942 |
| PLK-50 | 51 183 | GCAAGAAGGGCACAGUUU AAACUGUGCCCUUUCUUGC | 724-742 | 947-965 |
| PLK-51 | 52 184 | GAAAGGGCACAGUUUCGAG CUCGAAACUGUGCCCUUUC | 728-746 | 951-969 |
| PLK-54 | 55 187 | GGUGUAUCAUGUAUACCUU AAGGUAUACAUGAUACACC | 766-784 | 989-1007 |
| PLK-55 | 56 188 | AUCAUGUAUACCUUGUUAG CUAACAAGGUAUACAUGAU | 771-789 | 994-1012 |
| PLK-56 | 57 189 | AUGUAUACCUUGUUAGUGG CCACUAACAAGGUAUACAU | 774-792 | 997-1015 |
| PLK-57 | 58 190 | AUACCUUGUUAGUGGGCAA UUGCCCACUAACAAGGUAU | 778-796 | 1001-1019 |
| PLK-58 | 59 191 | CUUGUUAGUGGGCAAACCA UGGUUUGCCCACUAACAAG | 782-800 | 1005-1023 |
| PLK-59 | 60 192 | UUUGAGACUUCUUGCCUAA UUAGGCAAGAAGUCUCAAA | 804-822 | 1027-1045 |
| PLK-60 | 61 193 | AGAGACCUACCUCCGGAUC GAUCCGGAGGUAGGUCUCU | 824-842 | 1047-1065 |
| PLK-61 | 62 194 | GAGACCUACCUCCGGAUCA UGAUCCGGAGGUAGGUCUC | 825-843 | 1048-1066 |
| PLK-62 | 63 195 | CCUCCGGAUCAAGAAGAAU AUUCUUCUUGAUCCGGAGG | 833-851 | 1056-1074 |
| PLK-63 | 64 196 | CCGGAUCAAGAAGAAUGAA UUCAUUCUUCUUGAUCCGG | 836-854 | 1059-1077 |
| PLK-64 | 65 197 | CGGAUCAAGAAGAAUGAAU AUUCAUUCUUCUUGAUCCG | 837-855 | 1060-1078 |
| PLK-65 | 66 198 | GGAUCAAGAAGAAUGAAUA UAUUCAUUCUUCUUGAUCC | 838-856 | 1061-1079 |
| PLK-66 | 67 199 | GAUCAAGAAGAAUGAAUAC GUAUUCAUUCUUCUUGAUC | 839-857 | 1062-1080 |
| PLK-67 | 68 200 | CAAGAAGAAUGAAUACAGU ACUGUAUUCAUUCUUCUUG | 842-860 | 1065-1083 |
| PLK-68 | 69 201 | GAAGAAUGAAUACAGUAUU AAUACUGUAUUCAUUCUUC | 845-863 | 1068-1086 |
| PLK-69 | 70 202 | GAAUGAAUACAGUAUUCCC GGGAAUACUGUAUUCAUUC | 848-866 | 1071-1089 |
| PLK-70 | 71 203 | UGAAUACAGUAUUCCCAAG CUUGGGAAUACUGUAUUCA | 851-869 | 1074-1092 |
| PLK-71 | 72 204 | UACAGUAUUCCCAAGCACA UGUGCUUGGGAAUACUGUA | 855-873 | 1078-1096 |

TABLE 4-continued

Human-macaque homologous siRNA sequences

| No. | SEQ ID No. | Nucleotide sequence (5'→3') | Corresponding target site sequence in human mRNA (NM_005030.3) | Corresponding target site sequence in macaque mRNA (XM_001092070.2) |
|---|---|---|---|---|
| PLK-72 | 73<br>205 | GUAUUCCCAAGCACAUCAA<br>UUGAUGUGCUUGGGAAUAC | 859-877 | 1082-1100 |
| PLK-73 | 74<br>206 | GAUGCUUCAGACAGAUCCC<br>GGGAUCUGUCUGAAGCAUC | 905-923 | 1128-1146 |
| PLK-80 | 81<br>213 | GAGUUCUUUACUUCUGGCU<br>AGCCAGAAGUAAAGAACUC | 960-978 | 1183-1201 |
| PLK-81 | 82<br>214 | GUUCUUUACUUCUGGCUAU<br>AUAGCCAGAAGUAAAGAAC | 962-980 | 1185-1203 |
| PLK-82 | 83<br>215 | CUUUACUUCUGGCUAUAUC<br>GAUAUAGCCAGAAGUAAAG | 965-983 | 1188-1206 |
| PLK-84 | 85<br>217 | CCCUCACAGUCCUCAAUAA<br>UUAUUGAGGACUGUGAGGG | 1069-1087 | 1292-1310 |
| PLK-85 | 86<br>218 | CCUCACAGUCCUCAAUAAA<br>UUUAUUGAGGACUGUGAGG | 1070-1088 | 1293-1311 |
| PLK-86 | 87<br>219 | CAGUCCUCAAUAAAGGCUU<br>AAGCCUUUAUUGAGGACUG | 1075-1093 | 1298-1316 |
| PLK-87 | 88<br>220 | CUCAAUAAAGGCUUGGAGA<br>UCUCCAAGCCUUUAUUGAG | 1080-1098 | 1303-1321 |
| PLK-88 | 89<br>221 | UCAAUAAAGGCUUGGAGAA<br>UUCUCCAAGCCUUUAUUGA | 1081-1099 | 1304-1322 |
| PLK-89 | 90<br>222 | CAAUAAAGGCUUGGAGAAC<br>GUUCUCCAAGCCUUUAUUG | 1082-1100 | 1305-1323 |
| PLK-90 | 91<br>223 | UAAAGGCUUGGAGAACCCC<br>GGGGUUCUCCAAGCCUUUA | 1085-1103 | 1308-1326 |
| PLK-92 | 93<br>225 | GAACCAGUGGUUCGAGAGA<br>UCUCUCGAACCACUGGUUC | 1131-1149 | 1354-1372 |
| PLK-93 | 94<br>226 | CCAGUGGUUCGAGAGACAG<br>CUGUCUCUCGAACCACUGG | 1134-1152 | 1357-1375 |
| PLK-94 | 95<br>227 | AGACAGGUGAGGUGGUCGA<br>UCGACCACCUCACCUGUCU | 1147-1165 | 1370-1388 |
| PLK-95 | 96<br>228 | GGCAAGAGGAGGCUGAGGA<br>UCCUCAGCCUCCUCUUGCC | 1240-1258 | 1463-1481 |
| PLK-96 | 97<br>229 | GCAAGAGGAGGCUGAGGAU<br>AUCCUCAGCCUCCUCUUGC | 1241-1259 | 1464-1482 |
| PLK-97 | 98<br>230 | AAGAGGAGGCUGAGGAUCC<br>GGAUCCUCAGCCUCCUCUU | 1243-1261 | 1466-1484 |
| PLK-98 | 99<br>231 | CCAUCUUCUGGGUCAGCAA<br>UUGCUGACCCAGAAGAUGG | 1273-1291 | 1496-1514 |
| PLK-99 | 100<br>232 | UCAGCAAGUGGGUGGACUA<br>UAGUCCACCCACUUGCUGA | 1285-1303 | 1508-1526 |
| PLK-100 | 101<br>233 | CAGCAAGUGGGUGGACUAU<br>AUAGUCCACCCACUUGCUG | 1286-1304 | 1509-1527 |
| PLK-101 | 102<br>234 | GCAAGUGGGUGGACUAUUC<br>GAAUAGUCCACCCACUUGC | 1288-1306 | 1511-1529 |
| PLK-102 | 103<br>235 | GGACUAUUCGGACAAGUAC<br>GUACUUGUCCGAAUAGUCC | 1298-1316 | 1521-1539 |
| PLK-103 | 104<br>236 | GGUAUCAGCUCUGUGAUAA<br>UUAUCACAGAGCUGAUACC | 1324-1342 | 1547-1565 |
| PLK-104 | 105<br>237 | GGUGCUCUUCAAUGACUCA<br>UGAGUCAUUGAAGAGCACC | 1352-1370 | 1575-1593 |

TABLE 4-continued

Human-macaque homologous siRNA sequences

| No. | SEQ ID No. | Nucleotide sequence (5'→3') | Corresponding target site sequence in human mRNA (NM_005030.3) | Corresponding target site sequence in macaque mRNA (XM_001092070.2) |
|---|---|---|---|---|
| PLK-105 | 106 238 | GCUCUUCAAUGACUCAACA UGUUGAGUCAUUGAAGAGC | 1355-1373 | 1578-1596 |
| PLK-106 | 107 239 | UGACUCAACACGCCUCAUC GAUGAGGCGUGUUGAGUCA | 1364-1382 | 1587-1605 |
| PLK-107 | 108 240 | CACGCCUCAUCCUCUACAA UUGUAGAGGAUGAGGCGUG | 1372-1390 | 1595-1613 |
| PLK-109 | 110 242 | GGUGACAGCCUGCAGUACA UGUACUGCAGGCUGUCACC | 1395-1413 | 1618-1636 |
| PLK-110 | 111 243 | GUGACAGCCUGCAGUACAU AUGUACUGCAGGCUGUCAC | 1396-1414 | 1619-1637 |
| PLK-111 | 112 244 | CCCAACUCCUUGAUGAAGA UCUUCAUCAAGGAGUUGGG | 1458-1476 | 1681-1699 |
| PLK-112 | 113 245 | CCAACUCCUUGAUGAAGAA UUCUUCAUCAAGGAGUUGG | 1459-1477 | 1682-1700 |
| PLK-113 | 114 246 | ACUCCUUGAUGAAGAAGAU AUCUUCUUCAUCAAGGAGU | 1462-1480 | 1685-1703 |
| PLK-114 | 115 247 | CUCCUUGAUGAAGAAGAUC GAUCUUCUUCAUCAAGGAG | 1463-1481 | 1686-1704 |
| PLK-115 | 116 248 | GAAGAAGAUCACCCUCCUU AAGGAGGGUGAUCUUCUUC | 1472-1490 | 1695-1713 |
| PLK-116 | 117 249 | GAAGAUCACCCUCCUUAAA UUUAAGGAGGGUGAUCUUC | 1475-1493 | 1698-1716 |
| PLK-117 | 118 250 | GAUCACCCUCCUUAAAUAU AUAUUUAAGGAGGGUGAUC | 1478-1496 | 1701-1719 |
| PLK-118 | 119 251 | AUAUUCCGCAAUUACAUG CAUGUAAUUGCGGAAAUAU | 1493-1511 | 1716-1734 |
| PLK-120 | 121 253 | GCAGCGUGCAGAUCAACUU AAGUUGAUCUGCACGCUGC | 1636-1654 | 1859-1877 |
| PLK-121 | 122 254 | GCGUGCAGAUCAACUUCUU AAGAAGUUGAUCUGCACGC | 1639-1657 | 1862-1880 |
| PLK-122 | 123 255 | AGAUCAACUUCUUCCAGGA UCCUGGAAGAAGUUGAUCU | 1645-1663 | 1868-1886 |
| PLK-123 | 124 256 | GAUCAACUUCUUCCAGGAU AUCCUGGAAGAAGUUGAUC | 1646-1664 | 1869-1887 |
| PLK-124 | 125 257 | UCAACUUCUUCCAGGAUCA UGAUCCUGGAAGAAGUUGA | 1648-1666 | 1871-1889 |
| PLK-125 | 126 258 | CUUCUUCCAGGAUCACACC GGUGUGAUCCUGGAAGAAG | 1652-1670 | 1875-1893 |
| PLK-126 | 127 259 | GAUCACACCAAGCUCAUCU AGAUGAGCUUGGUGUGAUC | 1662-1680 | 1885-1903 |
| PLK-127 | 128 260 | UGAUGGCAGCCGUGACCUA UAGGUCACGGCUGCCAUCA | 1690-1708 | 1913-1931 |
| PLK-128 | 129 261 | GCAGAGCUGCAUCAUCCUU AAGGAUGAUGCAGCUCUGC | 1982-2000 | 2205-2223 |
| PLK-129 | 130 262 | CCCACCAUAUGAAUUGUAC GUACAAUUCAUAUGGUGGG | 2081-2099 | 2303-2321 |
| PLK-130 | 131 263 | CCACCAUAUGAAUUGUACA UGUACAAUUCAUAUGGUGG | 2082-2100 | 2304-2322 |

TABLE 4-continued

Human-macaque homologous siRNA sequences

| No. | SEQ ID No. | Nucleotide sequence (5'→3') | Corresponding target site sequence in human mRNA (NM_005030.3) | Corresponding target site sequence in macaque mRNA (XM_001092070.2) |
|---|---|---|---|---|
| PLK-131 | 132<br>264 | CACCAUAUGAAUUGUACAG<br>CUGUACAAUUCAUAUGGUG | 2083-2101 | 2305-2323 |

TABLE 5

Human-chimpanzee homologous siRNA sequences

| No. | SEQ ID No. | Nucleotide sequence (5'→3') | Corresponding target site sequence in human mRNA (NM_005030.3) | Corresponding target site sequence in chimpanzee mRNA (XM_001163623.2) |
|---|---|---|---|---|
| PLK-2 | 3<br>135 | CCAAGUGCUUCGAGAUCUC<br>GAGAUCUCGAAGCACUUGG | 247-265 | 885-903 |
| PLK-3 | 4<br>136 | GUGCUUCGAGAUCUCGGAC<br>GUCCGAGAUCUCGAAGCAC | 251-269 | 889-907 |
| PLK-5 | 6<br>138 | CAAGAUUGUGCCUAAGUCU<br>AGACUUAGGCACAAUCUUG | 296-314 | 934-952 |
| PLK-6 | 7<br>139 | GAUUGUGCCUAAGUCUCUG<br>CAGAGACUUAGGCACAAUC | 299-317 | 937-955 |
| PLK-8 | 9<br>141 | AAGCCGCACCAGAGGGAGA<br>UCUCCCUCUGGUGCGGCUU | 324-342 | 962-980 |
| PLK-9 | 10<br>142 | GAUGUCCAUGGAAAUAUCC<br>GGAUAUUUCCAUGGACAUC | 344-362 | 982-1000 |
| PLK-10 | 11<br>143 | AUGGAAAUAUCCAUUCACC<br>GGUGAAUGGAUAUUUCCAU | 351-369 | 989-1007 |
| PLK-11 | 12<br>144 | GAAAUAUCCAUUCACCGCA<br>UGCGGUGAAUGGAUAUUUC | 354-372 | 992-1010 |
| PLK-12 | 13<br>145 | AUAUCCAUUCACCGCAGCC<br>GGCUGCGGUGAAUGGAUAU | 357-375 | 995-1013 |
| PLK-13 | 14<br>146 | ACCAGCACGUCGUAGGAUU<br>AAUCCUACGACGUGCUGGU | 382-400 | 1020-1038 |
| PLK-14 | 15<br>147 | UCGUAGGAUUCCACGGCUU<br>AAGCCGUGGAAUCCUACGA | 391-409 | 1029-1047 |
| PLK-15 | 16<br>148 | CGUAGGAUUCCACGGCUUU<br>AAAGCCGUGGAAUCCUACG | 392-410 | 1030-1048 |
| PLK-16 | 17<br>149 | CGACUUCGUGUUCGUGGUG<br>CACCACGAACACGAAGUCG | 422-440 | 1060-1078 |
| PLK-17 | 18<br>150 | ACUUCGUGUUCGUGGUGUU<br>AACACCACGAACACGAAGU | 424-442 | 1062-1080 |
| PLK-18 | 19<br>151 | GCUGCACAAGAGGAGGAAA<br>UUUCCUCCUCUUGUGCAGC | 473-491 | 1111-1129 |
| PLK-19 | 20<br>152 | CUGCACAAGAGGAGGAAAG<br>CUUUCCUCCUCUUGUGCAG | 474-492 | 1112-1130 |
| PLK-21 | 22<br>154 | CCGAUACUACCUACGGCAA<br>UUGCCGUAGGUAGUAUCGG | 512-530 | 1150-1168 |
| PLK-22 | 23<br>155 | CGAUACUACCUACGGCAAA<br>UUUGCCGUAGGUAGUAUCG | 513-531 | 1151-1169 |
| PLK-23 | 24<br>156 | GAUACUACCUACGGCAAAU<br>AUUUGCCGUAGGUAGUAUC | 514-532 | 1152-1170 |
| PLK-24 | 25<br>157 | CCUACGGCAAAUUGUGCUU<br>AAGCACAAUUUGCCGUAGG | 521-539 | 1159-1177 |

TABLE 5-continued

Human-chimpanzee homologous siRNA sequences

| No. | SEQ ID No. | Nucleotide sequence (5'→3') | Corresponding target site sequence in human mRNA (NM_005030.3) | Corresponding target site sequence in chimpanzee mRNA (XM_001163623.2) |
|---|---|---|---|---|
| PLK-25 | 26<br>158 | AUUGUGCUUGGCUGCCAGU<br>ACUGGCAGCCAAGCACAAU | 531-549 | 1169-1187 |
| PLK-26 | 27<br>159 | GCCAGUACCUGCACCGAAA<br>UUUCGGUGCAGGUACUGGC | 544-562 | 1182-1200 |
| PLK-27 | 28<br>160 | CUGCACCGAAACCGAGUUA<br>UAACUCGGUUUCGGUGCAG | 552-570 | 1190-1208 |
| PLK-28 | 29<br>161 | GCACCGAAACCGAGUUAUU<br>AAUAACUCGGUUUCGGUGC | 554-572 | 1192-1210 |
| PLK-33 | 34<br>166 | GAGACCUCAAGCUGGGCAA<br>UUGCCCAGCUUGAGGUCUC | 577-595 | 1215-1233 |
| PLK-34 | 35<br>167 | UGAAUGAAGAUCUGGAGGU<br>ACCUCCAGAUCUUCAUUCA | 604-622 | 1242-1260 |
| PLK-35 | 36<br>168 | GAAUGAAGAUCUGGAGGUG<br>CACCUCCAGAUCUUCAUUC | 605-623 | 1243-1261 |
| PLK-36 | 37<br>169 | AUGAAGAUCUGGAGGUGAA<br>UUCACCUCCAGAUCUUCAU | 607-625 | 1245-1263 |
| PLK-37 | 38<br>170 | UGAAGAUCUGGAGGUGAAA<br>UUUCACCUCCAGAUCUUCA | 608-626 | 1246-1264 |
| PLK-38 | 39<br>171 | GGCAACCAAAGUCGAAUAU<br>AUAUUCGACUUUGGUUGCC | 644-662 | 1282-1300 |
| PLK-39 | 40<br>172 | CAACCAAAGUCGAAUAUGA<br>UCAUAUUCGACUUUGGUUG | 646-664 | 1284-1302 |
| PLK-40 | 41<br>173 | ACCAAAGUCGAAUAUGACG<br>CGUCAUAUUCGACUUUGGU | 648-666 | 1286-1304 |
| PLK-41 | 42<br>174 | CCAAAGUCGAAUAUGACGG<br>CCGUCAUAUUCGACUUUGG | 649-667 | 1287-1305 |
| PLK-42 | 43<br>175 | AGUCGAAUAUGACGGGGAG<br>CUCCCCGUCAUAUUCGACU | 653-671 | 1291-1309 |
| PLK-43 | 44<br>176 | UAUGACGGGGAGAGGAAGA<br>UCUUCCUCUCCCCGUCAUA | 660-678 | 1298-1316 |
| PLK-44 | 45<br>177 | CUGUGUGGGACUCCUAAUU<br>AAUUAGGAGUCCCACACAG | 684-702 | 1322-1340 |
| PLK-45 | 46<br>178 | GUGGGACUCCUAAUUACAU<br>AUGUAAUUAGGAGUCCCAC | 688-706 | 1326-1344 |
| PLK-46 | 47<br>179 | UGGGACUCCUAAUUACAUA<br>UAUGUAAUUAGGAGUCCCA | 689-707 | 1327-1345 |
| PLK-47 | 48<br>180 | GACUCCUAAUUACAUAGCU<br>AGCUAUGUAAUUAGGAGUC | 692-710 | 1330-1348 |
| PLK-48 | 49<br>181 | CUAAUUACAUAGCUCCCGA<br>UCGGGAGCUAUGUAAUUAG | 697-715 | 1335-1353 |
| PLK-49 | 50<br>182 | UUACAUAGCUCCCGAGGUG<br>CACCUCGGGAGCUAUGUAA | 701-719 | 1339-1357 |
| PLK-50 | 51<br>183 | GCAAGAAAGGGCACAGUUU<br>AAACUGUGCCCUUUCUUGC | 724-742 | 1362-1380 |
| PLK-51 | 52<br>184 | GAAAGGGCACAGUUUCGAG<br>CUCGAAACUGUGCCCUUUC | 728-746 | 1366-1384 |
| PLK-52 | 53<br>185 | CCAUUGGGUGUAUCAUGUA<br>UACAUGAUACACCCAAUGG | 760-778 | 1398-1416 |
| PLK-53 | 54<br>186 | CAUUGGGUGUAUCAUGUAU<br>AUACAUGAUACACCCAAUG | 761-779 | 1399-1417 |

TABLE 5-continued

Human-chimpanzee homologous siRNA sequences

| No. | SEQ ID No. | Nucleotide sequence (5'→3') | Corresponding target site sequence in human mRNA (NM_005030.3) | Corresponding target site sequence in chimpanzee mRNA (XM_001163623.2) |
|---|---|---|---|---|
| PLK-54 | 55 187 | GGUGUAUCAUGUAUACCUU AAGGUAUACAUGAUACACC | 766-784 | 1404-1422 |
| PLK-55 | 56 188 | AUCAUGUAUACCUUGUUAG CUAACAAGGUAUACAUGAU | 771-789 | 1409-1427 |
| PLK-56 | 57 189 | AUGUAUACCUUGUUAGUGG CCACUAACAAGGUAUACAU | 774-792 | 1412-1430 |
| PLK-57 | 58 190 | AUACCUUGUUAGUGGGCAA UUGCCCACUAACAAGGUAU | 778-796 | 1416-1434 |
| PLK-58 | 59 191 | CUUGUUAGUGGGCAAACCA UGGUUUGCCCACUAACAAG | 782-800 | 1420-1438 |
| PLK-59 | 60 192 | UUUGAGACUUCUUGCCUAA UUAGGCAAGAAGUCUCAAA | 804-822 | 1442-1460 |
| PLK-60 | 61 193 | AGAGACCUACCUCCGGAUC GAUCCGGAGGUAGGUCUCU | 824-842 | 1462-1480 |
| PLK-61 | 62 194 | GAGACCUACCUCCGGAUCA UGAUCCGGAGGUAGGUCUC | 825-843 | 1463-1481 |
| PLK-62 | 63 195 | CCUCCGGAUCAAGAAGAAU AUUCUUCUUGAUCCGGAGG | 833-851 | 1471-1489 |
| PLK-63 | 64 196 | CCGGAUCAAGAAGAAUGAA UUCAUUCUUCUUGAUCCGG | 836-854 | 1474-1492 |
| PLK-64 | 65 197 | CGGAUCAAGAAGAAUGAAU AUUCAUUCUUCUUGAUCCG | 837-855 | 1475-1493 |
| PLK-65 | 66 198 | GGAUCAAGAAGAAUGAAUA UAUUCAUUCUUCUUGAUCC | 838-856 | 1476-1494 |
| PLK-66 | 67 199 | GAUCAAGAAGAAUGAAUAC GUAUUCAUUCUUCUUGAUC | 839-857 | 1477-1495 |
| PLK-67 | 68 200 | CAAGAAGAAUGAAUACAGU ACUGUAUUCAUUCUUCUUG | 842-860 | 1480-1498 |
| PLK-68 | 69 201 | GAAGAAUGAAUACAGUAUU AAUACUGUAUUCAUUCUUC | 845-863 | 1483-1501 |
| PLK-69 | 70 202 | GAAUGAAUACAGUAUUCCC GGGAAUACUGUAUUCAUUC | 848-866 | 1486-1504 |
| PLK-70 | 71 203 | UGAAUACAGUAUUCCCAAG CUUGGGAAUACUGUAUUCA | 851-869 | 1489-1507 |
| PLK-71 | 72 204 | UACAGUAUUCCCAAGCACA UGUGCUUGGGAAUACUGUA | 855-873 | 1493-1511 |
| PLK-72 | 73 205 | GUAUUCCCAAGCACAUCAA UUGAUGUGCUUGGGAAUAC | 859-877 | 1497-1515 |
| PLK-73 | 74 206 | GAUGCUUCAGACAGAUCCC GGGAUCUGUCUGAAGCAUC | 905-923 | 1543-1561 |
| PLK-74 | 75 207 | CAACCAUUAACGAGCUGCU AGCAGCUCGUUAAUGGUUG | 934-952 | 1572-1590 |
| PLK-75 | 76 208 | CCAUUAACGAGCUGCUUAA UUAAGCAGCUCGUUAAUGG | 937-955 | 1575-1593 |
| PLK-80 | 81 213 | GAGUUCUUUACUUCUGGCU AGCCAGAAGUAAAGAACUC | 960-978 | 1598-1616 |
| PLK-81 | 82 214 | GUUCUUUACUUCUGGCUAU AUAGCCAGAAGUAAAGAAC | 962-980 | 1600-1618 |
| PLK-82 | 83 215 | CUUUACUUCUGGCUAUAUC GAUAUAGCCAGAAGUAAAG | 965-983 | 1603-1621 |

TABLE 5-continued

Human-chimpanzee homologous siRNA sequences

| No. | SEQ ID No. | Nucleotide sequence (5'→3') | Corresponding target site sequence in human mRNA (NM_005030.3) | Corresponding target site sequence in chimpanzee mRNA (XM_001163623.2) |
| --- | --- | --- | --- | --- |
| PLK-84 | 85<br>217 | CCCUCACAGUCCUCAAUAA<br>UUAUUGAGGACUGUGAGGG | 1069-1087 | 1707-1725 |
| PLK-85 | 86<br>218 | CCUCACAGUCCUCAAUAAA<br>UUUAUUGAGGACUGUGAGG | 1070-1088 | 1708-1726 |
| PLK-86 | 87<br>219 | CAGUCCUCAAUAAAGGCUU<br>AAGCCUUUAUUGAGGACUG | 1075-1093 | 1713-1731 |
| PLK-87 | 88<br>220 | CUCAAUAAAGGCUUGGAGA<br>UCUCCAAGCCUUUAUUGAG | 1080-1098 | 1718-1736 |
| PLK-88 | 89<br>221 | UCAAUAAAGGCUUGGAGAA<br>UUCUCCAAGCCUUUAUUGA | 1081-1099 | 1719-1737 |
| PLK-89 | 90<br>222 | CAAUAAAGGCUUGGAGAAC<br>GUUCUCCAAGCCUUUAUUG | 1082-1100 | 1720-1738 |
| PLK-90 | 91<br>223 | UAAAGGCUUGGAGAACCCC<br>GGGGUUCUCCAAGCCUUUA | 1085-1103 | 1723-1741 |
| PLK-91 | 92<br>224 | AGAAGAACCAGUGGUUCGA<br>UCGAACCACUGGUUCUUCU | 1127-1145 | 1765-1783 |
| PLK-92 | 93<br>225 | GAACCAGUGGUUCGAGAGA<br>UCUCUCGAACCACUGGUUC | 1131-1149 | 1769-1787 |
| PLK-93 | 94<br>226 | CCAGUGGUUCGAGAGACAG<br>CUGUCUCUCGAACCACUGG | 1134-1152 | 1772-1790 |
| PLK-94 | 95<br>227 | AGACAGGUGAGGUGGUCGA<br>UCGACCACCUCACCUGUCU | 1147-1165 | 1785-1803 |
| PLK-95 | 96<br>228 | GGCAAGAGGAGGCUGAGGA<br>UCCUCAGCCUCCUCUUGCC | 1240-1258 | 1878-1896 |
| PLK-96 | 97<br>229 | GCAAGAGGAGGCUGAGGAU<br>AUCCUCAGCCUCCUCUUGC | 1241-1259 | 1879-1897 |
| PLK-97 | 98<br>230 | AAGAGGAGGCUGAGGAUCC<br>GGAUCCUCAGCCUCCUCUU | 1243-1261 | 1881-1899 |
| PLK-98 | 99<br>231 | CCAUCUUCUGGGUCAGCAA<br>UUGCUGACCCAGAAGAUGG | 1273-1291 | 1911-1929 |
| PLK-99 | 100<br>232 | UCAGCAAGUGGGUGGACUA<br>UAGUCCACCCACUUGCUGA | 1285-1303 | 1923-1941 |
| PLK-100 | 101<br>233 | CAGCAAGUGGGUGGACUAU<br>AUAGUCCACCCACUUGCUG | 1286-1304 | 1924-1942 |
| PLK-101 | 102<br>234 | GCAAGUGGGUGGACUAUUC<br>GAAUAGUCCACCCACUUGC | 1288-1306 | 1926-1944 |
| PLK-102 | 103<br>235 | GGACUAUUCGGACAAGUAC<br>GUACUUGUCCGAAUAGUCC | 1298-1316 | 1936-1954 |
| PLK-103 | 104<br>236 | GGUAUCAGCUCUGUGAUAA<br>UUAUCACAGAGCUGAUACC | 1324-1342 | 1962-1980 |
| PLK-104 | 105<br>237 | GGUGCUCUUCAAUGACUCA<br>UGAGUCAUUGAAGAGCACC | 1352-1370 | 1990-2008 |
| PLK-105 | 106<br>238 | GCUCUUCAAUGACUCAACA<br>UGUUGAGUCAUUGAAGAGC | 1355-1373 | 1993-2011 |
| PLK-106 | 107<br>239 | UGACUCAACACGCCUCAUC<br>GAUGAGGCGUGUUGAGUCA | 1364-1382 | 2002-2020 |
| PLK-107 | 108<br>240 | CACGCCUCAUCCUCUACAA<br>UUGUAGAGGAUGAGGCGUG | 1372-1390 | 2010-2028 |
| PLK-108 | 109<br>241 | CUACAAUGAUGGUGACAGC<br>GCUGUCACCAUCAUUGUAG | 1385-1403 | 2023-2041 |

TABLE 5-continued

Human-chimpanzee homologous siRNA sequences

| No. | SEQ ID No. | Nucleotide sequence (5'→3') | Corresponding target site sequence in human mRNA (NM_005030.3) | Corresponding target site sequence in chimpanzee mRNA (XM_001163623.2) |
|---|---|---|---|---|
| PLK-109 | 110 242 | GGUGACAGCCUGCAGUACA UGUACUGCAGGCUGUCACC | 1395-1413 | 2033-2051 |
| PLK-110 | 111 243 | GUGACAGCCUGCAGUACAU AUGUACUGCAGGCUGUCAC | 1396-1414 | 2034-2052 |
| PLK-111 | 112 244 | CCCAACUCCUUGAUGAAGA UCUUCAUCAAGGAGUUGGG | 1458-1476 | 2096-2114 |
| PLK-112 | 113 245 | CCAACUCCUUGAUGAAGAA UUCUUCAUCAAGGAGUUGG | 1459-1477 | 2097-2115 |
| PLK-113 | 114 246 | ACUCCUUGAUGAAGAAGAU AUCUUCUUCAUCAAGGAGU | 1462-1480 | 2100-2118 |
| PLK-114 | 115 247 | CUCCUUGAUGAAGAAGAUC GAUCUUCUUCAUCAAGGAG | 1463-1481 | 2101-2119 |
| PLK-115 | 116 248 | GAAGAAGAUCACCCUCCUU AAGGAGGGUGAUCUUCUUC | 1472-1490 | 2110-2128 |
| PLK-116 | 117 249 | GAAGAUCACCCUCCUUAAA UUUAAGGAGGGUGAUCUUC | 1475-1493 | 2113-2131 |
| PLK-117 | 118 250 | GAUCACCCUCCUUAAAUAU AUAUUUAAGGAGGGUGAUC | 1478-1496 | 2116-2134 |
| PLK-118 | 119 251 | AUAUUCCGCAAUUACAUG CAUGUAAUUGCGGAAAUAU | 1493-1511 | 2131-2149 |
| PLK-119 | 120 252 | UUACAUGAGCGAGCACUUG CAAGUGCUCGCUCAUGUAA | 1505-1523 | 2143-2161 |
| PLK-120 | 121 253 | GCAGCGUGCAGAUCAACUU AAGUUGAUCUGCACGCUGC | 1636-1654 | 2274-2292 |
| PLK-121 | 122 254 | GCGUGCAGAUCAACUUCUU AAGAAGUUGAUCUGCACGC | 1639-1657 | 2277-2295 |
| PLK-122 | 123 255 | AGAUCAACUUCUUCCAGGA UCCUGGAAGAAGUUGAUCU | 1645-1663 | 2283-2301 |
| PLK-123 | 124 256 | GAUCAACUUCUUCCAGGAU AUCCUGGAAGAAGUUGAUC | 1646-1664 | 2284-2302 |
| PLK-124 | 125 257 | UCAACUUCUUCCAGGAUCA UGAUCCUGGAAGAAGUUGA | 1648-1666 | 2286-2304 |
| PLK-125 | 126 258 | CUUCUUCCAGGAUCACACC GGUGUGAUCCUGGAAGAAG | 1652-1670 | 2290-2308 |
| PLK-126 | 127 259 | GAUCACACCAAGCUCAUCU AGAUGAGCUUGGUGUGAUC | 1662-1680 | 2300-2318 |
| PLK-127 | 128 260 | UGAUGGCAGCCGUGACCUA UAGGUCACGGCUGCCAUCA | 1690-1708 | 2328-2346 |
| PLK-128 | 129 261 | GCAGAGCUGCAUCAUCCUU AAGGAUGAUGCAGCUCUGC | 1982-2000 | 2620-2638 |
| PLK-129 | 130 262 | CCCACCAUAUGAAUUGUAC GUACAAUUCAUAUGGUGGG | 2081-2099 | 2718-2736 |
| PLK-130 | 131 263 | CCACCAUAUGAAUUGUACA UGUACAAUUCAUAUGGUGG | 2082-2100 | 2719-2737 |
| PLK-131 | 132 264 | CACCAUAUGAAUUGUACAG CUGUACAAUUCAUAUGGUG | 2083-2101 | 2720-2738 |
| PLK-132 | 133 265 | UCCUUUCCUUGGCUUUAUG CAUAAAGCCAAGGAAAGGA | 2127-2145 | 2764-2782 |

The foregoing 132 siRNAs obtained by such design were further optimized. At this time, the following six aspects are considered: 1) the action targets of the selected siRNAs are required to be evenly distributed in the full-length sequence of the mRNA; 2) avoiding the action targets to locate in the complex secondary or tertiary structural domain of the mRNA; 3) the action target sequence of the siRNAs are located in the coding region of plk1 mRNA. The 5' non-coding region of plk1 mRNA only consists of 53 nucleotides. A sequence in this region may be blocked by translation regulatory protein and ribosome subunit bound to it, so it is not suitable to be used as an action target of siRNA. With respect to the targets in the coding region and the 3' noncoding region, the targets in the coding region should be preferably considered, and particularly, the targets should avoid to be located in the low-complex and length-variable region in the 3' noncoding region close to the poly(A) tail; 4) a sequence in which the $1^{st}$ base is G/C, the $13^{th}$ base is not G, and the $19^{th}$ base is A rather than G in the first single strand is preferred; 5) a sequence in which the $3^{rd}$ base is A and the $10^{th}$ base is U in the first single strand is preferred; and 6) single nucleotide polymorphism site should be avoided. Based on the above considerations, 14 siRNA sequences were finally preferably selected from the 132 designed siRNA sequences. The result is shown in Table 6.

Oligonucleotide single strands of the siRNAs were chemically synthesized by a method well known in the art. The sequences of the synthesized oligonucleotides are shown in Table 6. During synthesis, two deoxy-thymidine monophosphates (dTMP) dTdT (which are underlined in Table 6) were added to the 3'-end of the oligonucleotide single strands. The complementary oligonucleotide single strands were annealed to form a double-stranded RNA, with both ends of the double-stranded structure having a 3' protruding end of dTdT, respectively.

TABLE 6

| No. | SEQ ID No. | Nucleotide sequence (5'→3') | Corresponding target site sequence in human mRNA (NM_005030.3) |
|---|---|---|---|
| PLK-3 | 4 | GUGCUUCGAGAUCUCGGAC<u>dTdT</u> | 251-269 |
|  | 136 | GUCCGAGAUCUCGAAGCAC<u>dTdT</u> |  |
| PLK-16 | 17 | CGACUUCGUGUUCGUGGUG<u>dTdT</u> | 422-440 |
|  | 149 | CACCACGAACACGAAGUCG<u>dTdT</u> |  |
| PLK-37 | 38 | UGAAGAUCUGGAGGUGAAA<u>dTdT</u> | 608-626 |
|  | 170 | UUUCACCUCCAGAUCUUCA<u>dTdT</u> |  |
| PLK-41 | 42 | CCAAAGUCGAAUAUGACGG<u>dTdT</u> | 649-667 |
|  | 174 | CCGUCAUAUUCGACUUUGG<u>dTdT</u> |  |
| PLK-54 | 55 | GGUGUAUCAUGUAUACCUU<u>dTdT</u> | 766-774 |
|  | 187 | AAGGUAUACAUGAUACACC<u>dTdT</u> |  |
| PLK-64 | 65 | CGGAUCAAGAAGAAUGAAU<u>dTdT</u> | 837-855 |
|  | 197 | AUUCAUUCUUCUUGAUCCG<u>dTdT</u> |  |
| PLK-65 | 66 | GGAUCAAGAAGAAUGAAUA<u>dTdT</u> | 838-856 |
|  | 198 | UAUUCAUUCUUCUUGAUCC<u>dTdT</u> |  |
| PLK-67 | 68 | CAAGAAGAAUGAAUACAGU<u>dTdT</u> | 842-860 |
|  | 200 | ACUGUAUUCAUUCUUCUUG<u>dTdT</u> |  |
| PLK-76 | 77 | CGAGCUGCUUAAUGACGAG<u>dTdT</u> | 944-962 |
|  | 209 | CUCGUCAUUAAGCAGCUCG<u>dTdT</u> |  |
| PLK-92 | 93 | GAACCAGUGGUUCGAGAGA<u>dTdT</u> | 1131-1149 |
|  | 225 | UCUCUCGAACCACUGGUUC<u>dTdT</u> |  |
| PLK-102 | 103 | GGACUAUUCGGACAAGUAC<u>dTdT</u> | 1298-1316 |
|  | 235 | GUACUUGUCCGAAUAGUCC<u>dTdT</u> |  |
| PLK-103 | 104 | GGUAUCAGCUCUGUGAUAA<u>dTdT</u> | 1324-1342 |
|  | 236 | UUAUCACAGAGCUGAUACC<u>dTdT</u> |  |
| PLK-108 | 109 | CUACAAUGAUGGUGACAGC<u>dTdT</u> | 1385-1403 |
|  | 241 | GCUGUCACCAUCAUUGUAG<u>dTdT</u> |  |
| PLK-128 | 129 | GCAGAGCUGCAUCAUCCUU<u>dTdT</u> | 1982-2000 |
|  | 261 | AAGGAUGAUGCAGCUCUGC<u>dTdT</u> |  |

Example 2

Verification of the Inhibitory Effect of the siRNAs on the Expression of Plk1 Gene (Transfection of the siRNAs)

Human liver cancer cell strain HepG2 was seeded in a 24-well plate by using a DMEM complete medium containing 10% fetal bovine serum, 2 mM L-glutamine, 100 U/ml penicillin and 100 g/ml streptomycin. The density of cells was $4 \times 10^5$ cells/well and each well had 0.5 ml, and the cells were cultured at 37° C. overnight.

The detailed operating steps of transfection were as follows: Dilute 100 ng of the 14 siRNAs synthesized in Example 1 (PLK-3, 16, 37, 41, 54, 64, 65, 67, 76, 92, 102, 103, 108 and 128) in 50 μl DEME serum-free medium respectively, meanwhile dilute 1 μl Lipofectamine™ 2000 (made by Invitrogen) in 50 μl DEME serum-free medium, incubate the foregoing two solutions at room temperature for 5 min respectively, and then evenly mix them. After the mixed solution was allowed to stand at room temperature for 20 min, 100 μl of the mixed solution was added into the 24-well plate seeded with HepG2 cells. The final concentration of siRNA was about 10 nM. The cells were cultured at 37° C. for 4 h, then 1 ml DMEM complete medium containing 10% fetal bovine serum, 2 mM L-glutamine, 100 U/ml penicillin and 100 g/ml streptomycin was added, and the cells were cultured at 37° C. for 24 h. As a negative control, a negative control siRNA (N.C.siRNA) with a sense strand of 5'-UUCUCCGAACGUGUCACGUdTdT-3' (SEQ ID NO: 280) and a complementary antisense strand of 5'-ACGUGACACGUUCGGAGAAdTdT-3' (SEQ ID NO: 281) was transfected simultaneously.

(Inhibitory Effect of the siRNAs on the Expression Level of Plk1 mRNA)

The expression amount of plk1 mRNA in HepG2 cells transfected with siRNA PLK-3, 16, 37, 41, 54, 64, 65, 67, 76, 92, 102, 103, 108 and 128 respectively was detected by fluorescent Quantitative Real-Time PCR (qRT-PCR) comprising the following steps: after culturing the transfected cells for 24 h, total RNA in the cells was extracted with RNeasy mini Kit (made by Qiagen). The absorbance of $OD_{280}$ and $OD_{260}$ of the extracted RNA sample was determined by ultraviolet spectrophotometer, and the concentration of the RNA sample was calculated according to the following formula: RNA concentration (μg/μL)=0.04× $OD_{260}$×Dilution factor. Then cDNA was synthesized by using PrimeScript™ 1st Strand cDNA Synthesis Kit (made by Takara), wherein each sample used 2 μg total RNA extracted by the above steps. After synthesis of cDNA, SYBR® Premix Ex Taq™ (made by Takara) kit was used to perform fluorescent qRT-PCR reaction, wherein the PCR amplification primers used for amplifying plk1 and β-actin which was used as the internal control for the quantitative PCR reaction are shown in Table 7.

TABLE 7

|  | Upstream primer | Downstream primer |
| --- | --- | --- |
| plk1 | 5'-GCCCCTCACAGTCCTCAATA-3' (SEQ ID NO: 266) | 5'-TACCCAAGGCCGTACTTGTC-3' (SEQ ID NO: 267) |
| β-actin | 5'-AGCGAGCATCCCCCAAAGTT-3' (SEQ ID NO: 268) | 5'-GGGCACGAAGGCTCATCATT-3' (SEQ ID NO: 269) |

The inhibition rate of the siRNAs on the expression level of plk1 mRNA was calculated according to the following equation: the inhibition rate=[1−(the expression amount of plk1 mRNA in the experimental wells/the expression amount of β-actin mRNA in the experimental wells)/(the expression amount of plk1 mRNA in the negative control wells/the expression amount of β-actin mRNA in the negative control wells)]×100%. The result is shown in FIG. 1. It can be seen from FIG. 1 that, all the siRNAs of the present invention have an effect of inhibiting the expression level of plk1 mRNA, wherein the inhibition rates of siRNA PLK-65, siRNA PLK-67 and siRNA PLK-76 on the expression level of plk1 mRNA are 64%, 68% and 78% respectively, all above 60%, suggesting that the siRNAs of the present invention all have the activity of inhibiting the expression of plk1 gene and may be used to inhibit the expression of plk1 gene.

Preparation Example 1

Suzhou Ribo Life Science Co., Ltd. was entrusted to synthesize the oligonucleotides listed in Table 8. These oligonucleotides contain modified nucleotide groups. The complementary oligonucleotide strands were annealed to form modified siRNAs, named as PLK(m)-65-1, PLK(m)-65-2, PLK(m)-67-1, PLK(m)-67-2 and PLK(m)-76-1 respectively, wherein (OMe) means that the 2'-hydroxy of the pentose group in the nucleotide residue on its left is substituted by methoxy, while (F) means that the 2'-hydroxy of the pentose group in the nucleotide residue on its left is substituted by fluorine. The nucleotide sequences of these siRNAs before being modified correspond to PLK-65, PLK-67 and PLK-76 in Example 1 respectively.

TABLE 8

| No. | Nucleotide sequence (5'→3') |
|---|---|
| PLK(m)-65-1 | G(OMe)GAUC(OMe)A(OMe)AGAAGAAU(OMe)GAAUA(OMe)dTdT (SEQ ID NO: 270)<br>UA(OMc)UUCAUUCUUCUUG(OMc)AUCCdTdT (SEQ ID NO: 271) |
| PLK(m)-65-2 | G(OMe)GAUC(OMe)A(OMe)AGAAGAAU(OMe)GAAU(OMe)AdTdT (SEQ ID NO: 272)<br>UA(OMc)UUC(F)AUUCUUCUUGAU(F)CCdTdT (SEQ ID NO: 273) |
| PLK(m)-67-1 | C(OMe)A(OMe)AGAAGAAUGAAU(OMe)AC(OMe)AGUdTdT (SEQ ID NO: 274)<br>AC(OMe)UG(OMe)UAUUCAUUCUUCUU(F)GdTdT (SEQ ID NO: 275) |
| PLK(m)-67-2 | C(OMe)A(OMe)AGAAGAAUGAAU(OMe)AC(OMe)A(OMe)GUdTdT (SEQ ID NO: 276)<br>AC(OMe)U(F)GUAUUCAUUCUUCUU(F)GdTdT (SEQ ID NO: 277) |
| PLK(m)-76-1 | C(OMe)GAGCU(OMe)GCUUAAUG(OMe)ACGAGdTdT (SEQ ID NO: 278)<br>CU(OMe)CGUC(F)AUUAAGCAGCUCGdTdT (SEQ ID NO: 279) |

Example 3

Evaluation of the Influence of Chemical Modification on Serum Stability of the siRNAs With respect to PLK(m)-65-1, PLK(m)-65-2, PLK(m)-67-1, PLK(m)-67-2 and PLK(m)-76-1 obtained in Preparation Example 1 as well as PLK-65, PLK-67 and PLK-76 obtained in Example 1, their stability in serum environment was determined. And the detailed steps were as follows.

Figure 2:
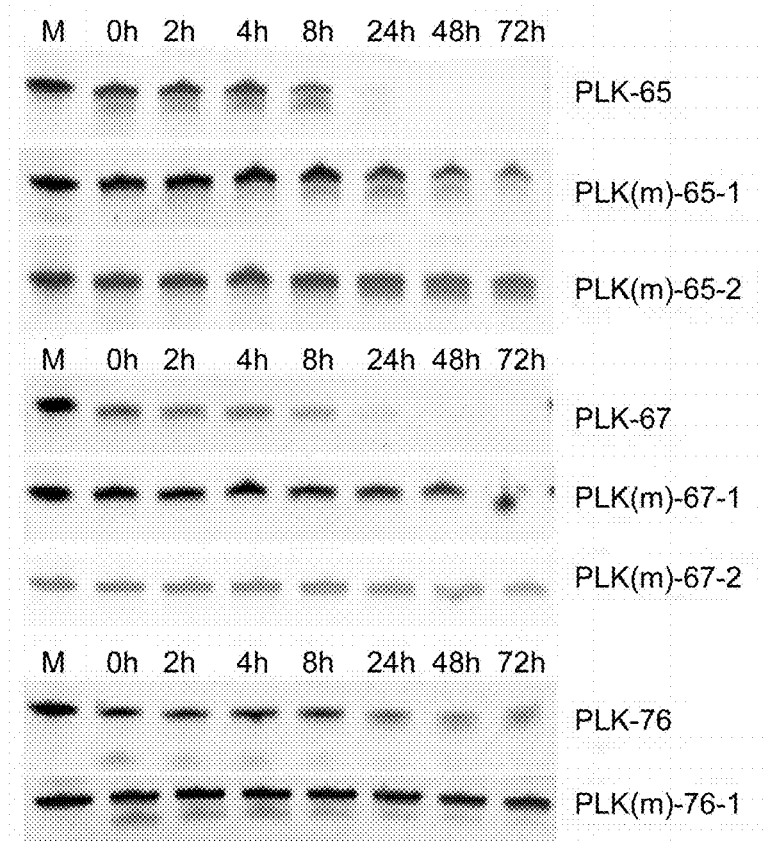
FIG. 2 shows the detection result of the serum stability of the siRNA in Example 3 before and after being chemically modified.

10 μl of the foregoing modified and unmodified siRNAs (20 μmol) were mixed with 50 μl fetal bovine serum (FBS, bought from HyClone, Cat. No. GTB0060) and 40 μl PBS respectively, and then incubated at 37° C. for 0, 2, 4, 8, 24, 48 and 72 h to obtain the treated samples. 10 μl of each of the treated samples was taken and subjected to 20% PAGE. Degradation rates were calculated based on the ratio between the light intensity of the electrophoretic bands of the above treated samples and the light intensity of the electrophoretic bands of the samples at 0 h. The results are shown in FIG. 2 and Table 9. The degradation rates listed in Table 9 are those calculated based on the ratio between the light intensity of the electrophoretic bands of the samples at 72 h and the light intensity of the electrophoretic bands of the samples at 0 h. It can be seen from FIG. 2 and Table 9 that, in serum environment, the stability of the modified siRNAs is obviously increased compared with that of the unmodified siRNAs.

TABLE 9

| Modified siRNA | Degradation rate (%) | Unmodified siRNA | Degradation rate (%) |
|---|---|---|---|
| PLK(m)-65-1 | 25.13 ± 3.71 | PLK-65 | 94.67 ± 2.87 |
| PLK(m)-65-2 | 10.98 ± 5.95 | | |
| PLK(m)-67-1 | 8.64 ± 2.24 | PLK-67 | 86.64 ± 5.21 |
| PLK(m)-67-2 | 5.71 ± 3.84 | | |
| PLK(m)-76-1 | 8.95 ± 5.74 | PLK-76 | 72.34 ± 3.53 |

Example 4

Figure 3:
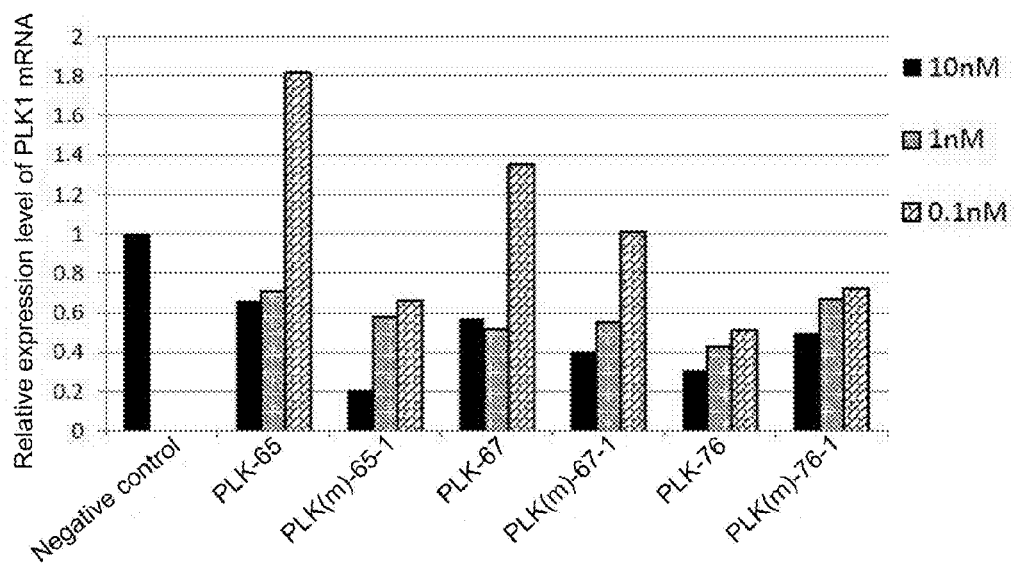
FIG. 3 shows the detection result of the inhibitory effect of the siRNA in Example 4 before and after being chemically modified on the expression level of plk1 mRNA.

Verification of the Inhibitory Effect of the siRNAs Before and after being Chemically Modified on the Expression Level of Plk1 mRNA The inhibitory effect of siRNA PLK(m)-65-1, siRNA PLK(m)-67-1 and siRNA PLK(m)-76-1 obtained in Preparation Example 1 as well as siRNA PLK-65, siRNA PLK-67 and siRNA PLK-76 obtained in Example 1 on the expression level of plk1 mRNA was determined by the method in Example 2, respectively. When performing the transfection, the foregoing siRNAs were transfected at gradient doses, such that the final concentrations of the foregoing siRNAs were 0.1 nM, 1 nM and 10 nM respectively. Negative control siRNA (NC.siRNA) with a sense strand of 5'-UUCUCCGAACGUGUCACGUdTdT-3' (SEQ ID NO: 280) and a complementary antisense strand of 5'-ACGUGACACGUUCGGAGAAdTdT-3' (SEQ ID NO: 281) which is the same as that in Example 2 was used as a negative control. The fluorescent qRT-PCR determination result is shown in FIG. 3. It can be seen from FIG. 3 that modified siRNAs have similar inhibitory effect on the expression level of plk1 mRNA compared to that of unmodified siRNAs. When the dose is 10 nM, PLK(m)-65-1 and PLK(m)-67-1 have more excellent inhibitory effect compared with that of unmodified siRNA PLK-65 and PLK-67. Apparently, such results are obtained because the modification enhances the stability of the siRNAs and thereby lengthening the retention time of the siRNAs in cells.

Example 5

Inhibition of Breast Cancer Cell Growth by Locally Administered siRNAs

Human breast cancer cell strain MDA-MB-435s was inoculated in situ under the fat pad of the second mammary gland of each BALB/c nude mouse ($5×10^6$ cells/nude mouse). About 14 days later, visible tumor was formed. The tumor volume was calculated according to the following formula: $V=0.5×a×b^2$, wherein a refers to the long diameter of the tumor and b refers to the short diameter of the tumor. Five inoculated nude mice formed a group. The average tumor volume of the nude mice in each group was about 50 mm³.

As the treatment groups, 10 μg siRNA PLK-65, PLK(m)-65-1, PLK(m)-65-2, PLK-67, PLK(m)-67-1, PLK(m)-67-2, PLK-76 and PLK(m)-76-1 were respectively dissolved in 100 μl PBS (pH 7.4) and intratumoral injection was conducted directly. As the negative control group, the negative control siRNA(N.C.siRNA, with a sense strand of 5'-UUCUCCGAACGUGUCACGUdTdT-3' (SEQ ID NO: 280) and a complementary antisense strand of 5'-ACGUGA- CACGUUCGGAGAAdTdT-3' (SEQ ID NO: 281)) mentioned in Example 2 was employed. Every other day, 10 µg of the foregoing siRNAs were used to conduct intratumoral injection again. 20 days after the first injection, tumor volume was measured using the above-mentioned method. The result is shown in Table 10.

TABLE 10

|  | Tumor volume (mm$^3$) |
|---|---|
| Negative control | 160 ± 20 |
| PLK-65 | 95 ± 10 |
| PLK(m)-65-1 | 60 ± 20 |
| PLK(m)-65-2 | 75 ± 15 |
| PLK-67 | 80 ± 20 |
| PLK(m)-67-1 | 80 ± 30 |
| PLK(m)-67-2 | 90 ± 15 |
| PLK-76 | 80 ± 25 |
| PLK(m)-76-1 | 75 ± 20 |

It can be known from Table 10 that, compared with the negative control group, tumor cell growth was significantly inhibited in all the treatment groups treated with PLK-65, PLK(m)-65-1, PLK(m)-65-2, PLK-67, PLK(m)-67-1, PLK(m)-67-2, PLK-76 and PLK(m)-76-1.

Example 6

Inhibition of Breast Cancer Cell Growth by the siRNA Pharmaceutical Compositions When Systemically Administered Via Tail Vein Injection (Preparation of the siRNA Pharmaceutical Compositions)

In this example, polyethylene glycol-polylactic acid diblock copolymer (PEG-PLA) and cationic lipid N,N-dihydroxyethyl-N-methyl-N-2-(cholesteryloxycarbonylamino) ethylammonium bromide (BHEM-Chol) were used to prepare the siRNA pharmaceutical compositions. The detailed preparation procedure referred to the method mentioned in Yang XZ., et al. *J. Cont. Release* 2011, 156(2):203. That is, 25 mg PEG$_{5000}$-PLA$_{25000}$ and 1 mg BHEM-Chol were dissolved in 0.5 mL chloroform. After siRNA (0.025 mL, 0.2 mg) water solution was added, the solution was ultrasonicated in an ice bath to form an initial emulsion; then the initial emulsion was added into 1.5 mL 1% polyvinyl alcohol (PVA) water solution. The obtained solution was emulsified with ultrasound in an ice bath to form an emulsion. The emulsion was added into 25 mL 0.3% PVA water solution. The organic solvent was removed by evaporation under reduced pressure. The precipitate was collected by centrifuge. The precipitate was re-suspended with water and collected by centrifuge twice to remove PVA, thereby obtaining a pharmaceutical composition containing siRNA. In the pharmaceutical composition obtained by the above steps, the weight ratio of each ingredient was siRNA/cationic lipid/polymer=0.2/1.0/25.0.

(Inhibition of Breast Cancer Cell Growth by the siRNA Pharmaceutical Compositions Administered Via Tail Vein Injection)

Figure 4:
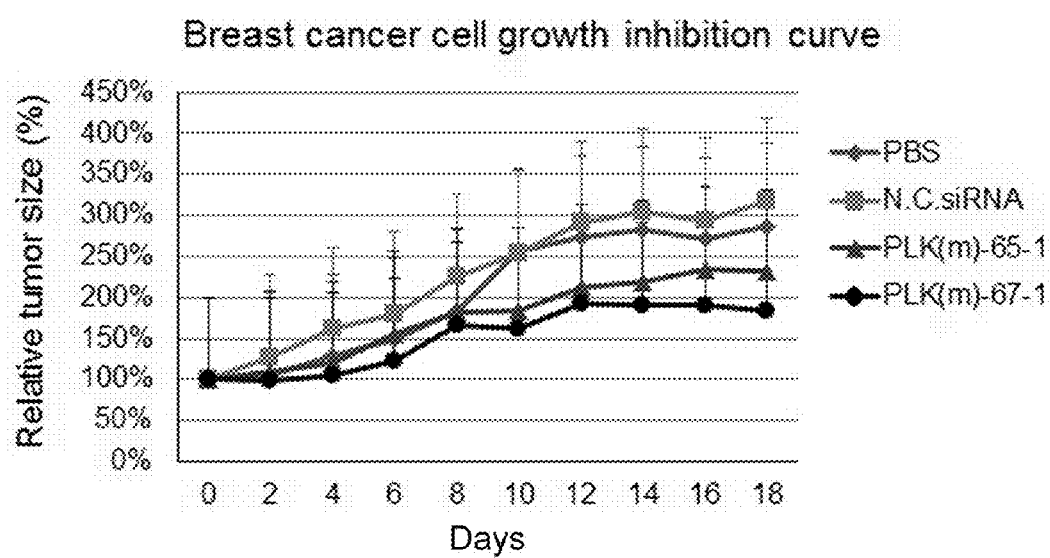
FIG. 4 shows the inhibitory effect of the pharmaceutical composition containing plk1 siRNA systemically administered via tail vein injection in Example 6 on the growth of breast cancer cells.

Human breast cancer cell strain MDA-MB-435s was inoculated in situ under the fat pad of the second mammary gland on the right of each BALB/c nude mouse (5×10$^6$ cells). About 14 days later, visible tumor was formed. The average tumor volume was about 50 mm$^3$. The nude mice were randomly divided into 4 groups, with each group having 8 nude mice. Administration was performed by tail vein injection. The administration dose was 1 mg/kg (~20 µg siRNA/mouse) calculated based on effective siRNA amount, and the administration was carried out every other day, 10 times in total. The negative control groups were injected via tail vein with 150 µl PBS solution (negative control group 1) and 150 µl PBS solution containing 20 µg negative control siRNA mentioned in Example 2 (the sense strand is 5'-UUCUCCGAACGUGUCACGUdTdT-3' (SEQ ID NO: 280) and the complementary antisense strand is 5'-ACGUGACACGUUCGGAGAAdTdT-3' (SEQ ID NO: 281) prepared by the above steps (NC. siRNA pharmaceutical composition, negative control group 2). The treatment groups were injected via tail vein with 150 µl PBS solution containing 20 µg PLK(m)-65-1 (PLK(m)-65-1 pharmaceutical composition, treatment group 1) or 150 µl PBS solution containing 20 µg PLK(m)-67-1 (PLK(m)-67-1 pharmaceutical composition, treatment group 2) prepared by the above steps. After each administration, the tumor size was measured to obtain tumor growth data. The tumor size was calculated according to the following formula: V=0.5×a×b$^2$, wherein a refers to the long diameter of the tumor and b refers to the short diameter of the tumor. When analyzing the result, the "average tumor size" of the mice in each group at the first administration (i.e., 0 day of drug administration) was defined as 100%. The standard deviation divided by the average tumor size gave relative standard deviation. In the subsequent administration process, the average tumor size and the standard deviation of each group measured each time were corrected with the average tumor size at day 0, such that a tumor cell growth inhibition curve as shown in FIG. 4 was obtained. It can be seen from FIG. 4 that, compared with the negative control groups, systemic administration of the pharmaceutical compositions containing PLK(m)-65-1 and PLK(m)-67-1 by tail vein injection may effectively promote apoptosis of breast cancer cells and inhibit growth of tumor tissues.

Example 7

Inhibition of Cervical Cancer Cell Growth by the siRNA Pharmaceutical Compositions Administered Via Tail Vein Injection (Preparation of the siRNA Pharmaceutical Compositions)

In this Example, polycaprolactone-poly(N,N-dimethylaminoethylmethacrylate) block copolymer (PCL-PDMAEMA) and polyethylene glycol-polyglutamic acid block copolymer in which the polyethylene glycol block is modified by folic acid (folate-PEG-PGA) were used to prepare the siRNA pharmaceutical compositions, wherein PCL-PDMAEMA is a poly β-amino ester amphiphilic cationic polymer, and PEG-PGA is an auxiliary polymer. The preparation steps of the siRNA pharmaceutical compositions referred to the method mentioned in Huang YY., et al. *Biomaterials*. 2012, (18):4653-. That is, 20 µl deionized water solution of siRNA (containing about 1 µg siRNA) and 50 µl PBS solution of PCL$_{5000}$-PDMAEMA$_{2000}$ were mixed. After the obtained solution was allowed to stand at room temperature for 20 min, 50 µl water solution of folate-PEG$_{5000}$-PGA$_{46000}$ was added and thoroughly mixed. After incubating at room temperature for 20 min, the system was adjusted by PBS to obtain the needed pharmaceutical composition, wherein the molar ratio of nitrogen (N) in PCL$_{5000}$-PDMAEMA$_{2000}$, phosphorus (P) in siRNA and carbon (C) in PEG$_{5000}$-PGA$_{46000}$ was 5:1:8.

(Inhibition of Cervical Cancer Cell Growth by the siRNA Pharmaceutical Compositions Administered Via Tail Vein Injection)

Figure 5:
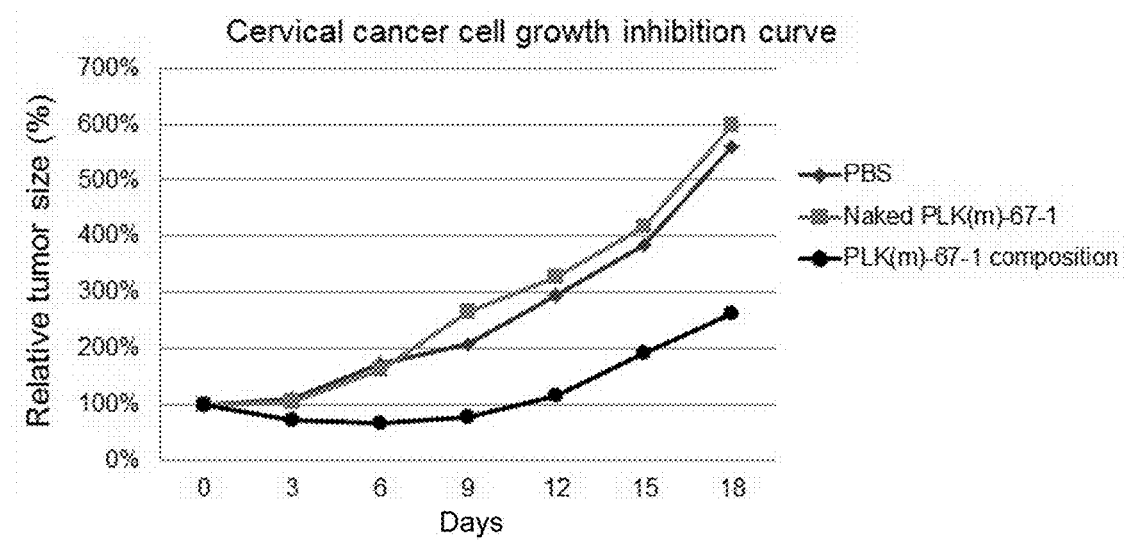
FIG. 5 shows the inhibitory effect of the pharmaceutical composition containing plk1 siRNA systemically administered via tail vein injection in Example 7 on the growth of cervical cancer cells.

Human cervical cancer cells Hela were inoculated subcutaneously in the right armpit of BALB/c nude mice ($5\times10^6$ cells). About 10 days later, visible tumor was formed. The average tumor volume was about 50 mm$^3$. The nude mice were randomly divided into 3 groups, with each group having 7 nude mice. Administration was performed by tail vein injection. The administration dose was 2 mg/kg (~40 siRNA/mouse) calculated based on effective siRNA amount, and the administration was carried out every three days, 7 times in total. The negative control groups were injected via tail vein with 200 µl blank PBS solution (negative control group 1) and PLK(m)-67-1 dissolved in 200 µl PBS (naked PLK(m)-67-1, negative control group 2). The treatment group was injected via tail vein with 200 µl PBS solution containing 40 µg PLK(m)-67-1 (PLK(m)-67-1 pharmaceutical composition, treatment group) prepared by the above steps. After each administration, the tumor size was measured to obtain tumor growth data. The tumor size was calculated according to the following formula: $V=0.5\times a\times b^2$, wherein a refers to the long diameter of the tumor and b refers to the short diameter of the tumor. When analyzing the result, the "average tumor size" of the mice in each group at the first administration (i.e., 0 day of drug administration) was defined as 100%. The standard deviation divided by the average tumor size gave relative standard deviation. In the subsequent administration process, the average tumor size and the standard deviation of each group measured each time were corrected with the average tumor size at day 0, such that a tumor cell growth inhibition curve as shown in FIG. 5 was obtained. It can be seen from FIG. 5 that, compared with the negative control groups, systemic administration of the pharmaceutical composition containing PLK (m)-67-1 by tail vein injection may effectively promote apoptosis of cervical cancer cells and inhibit growth of tumor tissues.

What is claimed is:

1. A siRNA with a double-stranded structure, the double-stranded structure consisting of a first single strand and a second single strand which are completely complementary, wherein,
the first single strand has a nucleotide sequence represented by SEQ ID NO: 77, which is the same as a target site sequence in a plk1 mRNA sequence represented by SEQ ID NO: 1; and
the second single strand complementary to the first single strand has a nucleotide sequence represented by SEQ ID NO: 209, which is complementary to the target site sequence in the plk1 mRNA sequence represented by SEQ ID NO: 1,
wherein each of the first single strand and the second single strand contains at least one modified nucleotide group respectively, wherein the modified nucleotide group is a nucleotide group in which the 2'-hydroxy of the ribose group is substituted by methoxy or fluorine,
wherein the siRNA is selected from the following:
PLK(m)-76-1 in which the first single strand is C(OMe)GAGCU(OMe)GCUUAAUG(OMe)ACGAGdTdT (SEC) ID NO: 278); and the second single strand is CU(OMe)CGUC(F)AUUAAGCAGCUCGdTdT (SEC) ID NO: 279),
wherein (OMe) means that the 2'-hydroxy of the pentose group in the nucleotide residue on its left is substituted by methoxy, while (F) means that the 2'-hydroxy of the pentose group in the nucleotide residue on its left is substituted by fluorine.

2. A pharmaceutical composition containing the siRNA according to claim 1 as a pharmaceutically active ingredient, as well as a cationic ingredient, a non-cationic ingredient and a pharmaceutically acceptable carrier.

3. The pharmaceutical composition according to claim 2, wherein
the cationic ingredient is at least one selected from the group consisting of N,N-dihydroxyethyl-N-methyl-N-2-(cholesteryloxycarbonylamino) ethylammonium bromide, (2,3-dioleoyloxy)propyl-trimethylammonium chloride, N-(1-(2,3-dioleoyloxy)propyl)-N,N,N-trimethylammonium chloride, polyethylenimine, poly β-amino ester and chitosan quaternary ammonium salt, and preferably is polycaprolactone-poly(N,N-dimethylaminoethylmethacrylate) block copolymer;
the non-cationic ingredient is at least one selected from the group consisting of polyethylene glycol-polylactic acid diblock copolymer, polyethylene glycol-polylactic acid triblock copolymer, polyethylene glycol-poly(lactic acid-glycolic acid) diblock copolymer and polyethylene glycol-poly(lactic acid-glycolic acid) triblock copolymer, and preferably is polyethylene glycol-polyglutamic acid block copolymer in which the polyethylene glycol block is modified by folic acid (folate-PEG-PGA); and the pharmaceutically acceptable carrier is selected from the group consisting of phosphate buffer solution with a pH of 4.0-9.0, tris(hydroxymethyl) aminomethane hydrochloride buffer solution with a pH of 7.5-8.5, normal saline, or 7-15 wt % sucrose solution.

4. A method for inhibiting the expression of plk1 gene in mammalian cells, wherein the method comprises introducing the siRNA according to claim 1 into mammalian cells, thereby allowing the siRNA to sequence-specifically induce inhibition of the expression of the plk1 gene.

5. The method according to claim 4, wherein modes for the introducing include introducing the siRNA directly, or introducing the siRNA in a form of the pharmaceutical composition,
wherein the pharmaceutical composition containing the siRNA as a pharmaceutically active ingredient further comprises a cationic ingredient, a non-cationic ingredient and a pharmaceutically acceptable carrier,
wherein the cationic ingredient comprises at least one of N,N-dihydroxyethyl-N-methyl-N-2-(cholesteryloxycarbonylamino) ethylammonium bromide, (2,3-dioleoyloxy)propyl-trimethylammonium chloride, N-(1-(2,3-dioleoyloxy)propyl)-N,N,N-trimethylammonium chloride, polyethylenimine, poly β-amino ester and chitosan quaternary ammonium salt, or polycaprolactone-poly(N,N-dimethylaminoethylmethacrylate) block copolymer,
wherein the non-cationic ingredient comprises at least one of polyethylene glycol-polylactic acid diblock copolymer, polyethylene glycol-polylactic acid triblock copolymer, polyethylene glycol-poly(lactic acid-glycolic acid) diblock copolymer and polyethylene glycol-poly(lactic acid-glycolic acid) triblock copolymer, or polyethylene glycol-polyglutamic acid block copolymer in which the polyethylene glycol block is modified by folic acid (folate-PEG-PGA), and
wherein the pharmaceutically acceptable carrier comprises at least one of phosphate buffer solution with a pH of 4.0-9.0, tris(hydroxymethyl) aminomethane hydrochloride buffer solution with a pH of 7.5-8.5, normal saline, or 7-15 wt % sucrose solution.

6. A method for treating tumor, comprising administering a pharmaceutical composition according to claim 2 to a subject in need thereof.

7. The method according to claim 6, wherein the tumor is breast cancer, liver cancer, lung cancer, cervical cancer or colon cancer with abnormally high expression of plk1 gene.

8. A method for treating tumor, comprising administering an siRNA according to claim 1 to a subject in need thereof.

9. The method according to claim 8, wherein the tumor is breast cancer, liver cancer, lung cancer, cervical cancer or colon cancer with abnormally high expression of plk1 gene.

* * * * *

UNITED STATES PATENT AND TRADEMARK OFFICE
CERTIFICATE OF CORRECTION

PATENT NO. : 9,593,335 B2  
APPLICATION NO. : 15/130091  
DATED : March 14, 2017  
INVENTOR(S) : Hongyan Zhang Page 1 of 1

It is certified that error appears in the above-identified patent and that said Letters Patent is hereby corrected as shown below:

In the Claims

In Column 147, Lines 35-37, in Claim 1, please delete "(SEC) ID NO: 278); and the second single stand is CU(OMe)CGUC(F)AUUAAGCAGCUCGdTdT (SEC) ID NO: 279)" and insert --(SEQ ID NO: 278); and the second single stand is CU(OMe)CGUC(F)AUUAAGCAGCUCGdTdT (SEQ ID NO: 279)-- therefor.

Signed and Sealed this  
Twenty-third Day of May, 2017

Michelle K. Lee  
*Director of the United States Patent and Trademark Office*

SEQUENCE LISTING

```
<160> NUMBER OF SEQ ID NOS: 281

<210> SEQ ID NO 1
<211> LENGTH: 2204
<212> TYPE: RNA
<213> ORGANISM: Homo sapiens

<400> SEQUENCE: 1
gagcggugcg gaggcucugc ucggaucgag gucugcagcg cagcuucggg agcaugagug      60
cugcagugac ugcagggaag cuggcacggg caccggccga cccugggaaa gccggggucc     120
ccggaguugc agcucccgga gcuccggcgg cggcuccacc ggcgaaagag aucccggagg     180
uccuagugga cccacgcagc cggcggcgcu augugcgggg ccgcuuuuug ggcaagggcg     240
gcuuugccaa gugcuucgag aucucggacg cggacaccaa ggagguguuc gcgggcaaga     300
uugugccuaa gucucugcug cucaagccgc accagaggga gaagaugucc auggaaauau     360
ccauucaccg cagccucgcc caccagcacg ucguaggauu ccacggcuuu uucgaggaca     420
acgacuucgu guucguggug uuggagcucu gccgccggag gucucuccug gagcugcaca     480
agaggaggaa agcccugacu gagccugagg cccgauacua ccuacggcaa auugugcuug     540
gcugccagua ccugcaccga aaccgaguua uucaucgaga ccucaagcug ggcaaccuuu     600
uccugaauga agaucuggag gugaaaauag gggauuuugg acuggcaacc aaagucgaau     660
augacgggga gaggaagaag acccugugug ggacuccuaa uuacauagcu cccgaggugc     720
ugagcaagaa agggcacagu uucgaggugg augugggucc cauggguu aucauguaua     780 ccuuguuagu gggcaaacca ccuuuugaga cuucuugccu aaaagagacc uaccucgga     840 ucaagaagaa ugaauacagu auucccaagc acaucaaccc cguggccgcc ucccucaucc     900
agaagaugcu ucagacagau cccacugccc gcccaaccau uaacgagcug cuuaaugacg     960
aguucuuuac uucuggcuau auccugcc gucuccca caccugccug accauuccac     1020
caagguuuuc gauugcuccc agcagccugg acccagcaa ccggaagccc cucacagucc     1080
ucaauaaagg cuuggagaac ccccugccug agcguccccg ggaaaaagaa gaaccagugg     1140
uucgagagac aggugaggug gucgacugcc accacuga caugcugcag cagcugcaca     1200
gugucaaugc cuccaagccc ucggagcgug ggcuggucga gcaagaggag gcugaggauc     1260
cugccugcau ccccaucuuc ugggucagca aguggggga cuauucggac aaguacgcc     1320
```

```
uugggυαuca gcucugugau aacagcgugg gggugcucuu caaugacuca acacgccuca     1380
uccucuacaa ugauggugac agccugcagu acauagagcg ugacggcacu gaguccuacc     1440
ucaccgugag uucccauccc aacuccuuga ugaagaagau cacccuccuu aaauauuucc     1500
gcaauuacau gagcgagcac uugcugaagg caggugccaa caucacgccg cgcgaaggug     1560
augagcucgc ccggcugccc uaccuacgga ccugguuccg cacccgcagc gccaucaucc     1620
ugcaccucag caacggcagc gugcagauca acuucuucca ggaucacacc aagcucaucu     1680
ugugcccacu gauggcagcc gugaccuaca ucgacgagaa gcgggacuuc cgcacauacc     1740
gccugagucu ccuggaggag uacggcgcgc gcaaggagcu ggccagccgg cuccgcuacg     1800
cccgcacuau gguggacaag cugcugagcu cacgcucggc cagcaaccgu cucaaggccu     1860
ccuaauagcu gcccucccu ccggacuggu gcccuccuca cucccaccug caucuggggc      1920
ccauacuggu uggcucccgc ggugccaugu cugcagugug cccccagcc ccgguggcug      1980 ggcagagcug caucauccuu gcagguggg guugcugugu aaguuauuuu uguacauguu      2040
cggguguggg uucuacagcc uugucccccu ccccucaac cccaccauau gaauuguaca     2100
gaauauuucu auugaauucg gaacugccu uuccuuggcu uuaugcacau uaaacagaug      2160
ugaauauuca aaaaaaaaa aaaaaaaaaa aaaaaaaaa aaaa                        2204

<210> SEQ ID NO 2
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 2
gcuccaccgg cgaaagaga                                                    19

<210> SEQ ID NO 3
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 3
ccaagugcuu cgagaucuc                                                    19

<210> SEQ ID NO 4
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 4
gugcuucgag aucucggac                                                    19

<210> SEQ ID NO 5
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde
```

```
<400> SEQUENCE: 5
ucucggacgc ggacaccaa                                                    19

<210> SEQ ID NO 6
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 6
caagauugug ccuaagucu                                                    19

<210> SEQ ID NO 7
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 7
gauugugccu aagucucug                                                    19

<210> SEQ ID NO 8
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 8
cuaagucucu gcugcucaa                                                    19

<210> SEQ ID NO 9
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 9
aagccgcacc agagggaga                                                    19

<210> SEQ ID NO 10
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 10
gauguccaug gaaauaucc                                                    19

<210> SEQ ID NO 11
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 11
```
auggaaauau ccauucacc                                                19

<210> SEQ ID NO 12
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 12
gaaauauuca uucaccgca                                                19

<210> SEQ ID NO 13
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 13
auauccauuc accgcagcc                                                19

<210> SEQ ID NO 14
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 14
accagcacgu cguaggauu                                                19

<210> SEQ ID NO 15
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 15
ucguaggauu ccacggcuu                                                19

<210> SEQ ID NO 16
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 16
cguaggauuc cacggcuuu                                                19

<210> SEQ ID NO 17
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 17

```
cgacuucgug uucguggug                                              19
```

<210> SEQ ID NO 18
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 18

```
acuucguguu cgugguguu                                              19
```

<210> SEQ ID NO 19
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 19

```
gcugcacaag aggaggaaa                                              19
```

<210> SEQ ID NO 20
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 20

```
cugcacaaga ggaggaaag                                              19
```

<210> SEQ ID NO 21
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 21

```
ggaggaaagc ccugacuga                                              19
```

<210> SEQ ID NO 22
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 22

```
ccgauacuac cuacggcaa                                              19
```

<210> SEQ ID NO 23
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 23

```
cgauacuacc uacggcaaa                                              19
```

<210> SEQ ID NO 24
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 24
gauacuaccu acggcaaau                                                    19

<210> SEQ ID NO 25
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 25
ccuacggcaa auugugcuu                                                    19

<210> SEQ ID NO 26
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 26
auugugcuug gcugccagu                                                    19

<210> SEQ ID NO 27
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 27
gccaguaccu gcaccgaaa                                                    19

<210> SEQ ID NO 28
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 28
cugcaccgaa accgaguua                                                    19

<210> SEQ ID NO 29
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 29
gcaccgaaac cgaguuauu                                                    19

```
<210> SEQ ID NO 30
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 30
ccgaaaccga guuauucau                                                19

<210> SEQ ID NO 31
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 31
aaaccgaguu auucaucga                                                19

<210> SEQ ID NO 32
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 32
accgaguuau ucaucgaga                                                19

<210> SEQ ID NO 33
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 33
aguuauucau cgagaccuc                                                19

<210> SEQ ID NO 34
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 34
gagaccucaa gcugggcaa                                                19

<210> SEQ ID NO 35
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 35
ugaaugaaga ucuggaggu                                                19
```

```
<210> SEQ ID NO 36
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 36
gaaugaagau cuggaggug                                                    19

<210> SEQ ID NO 37
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 37
augaagaucu ggaggugaa                                                    19

<210> SEQ ID NO 38
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 38
ugaagaucug gaggugaaa                                                    19

<210> SEQ ID NO 39
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 39
ggcaaccaaa gucgaauau                                                    19

<210> SEQ ID NO 40
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 40
caaccaaagu cgaauauga                                                    19

<210> SEQ ID NO 41
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 41
accaaagucg aauaugacg                                                    19

<210> SEQ ID NO 42
```

<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 42
ccaaagucga auaugacgg                                              19

<210> SEQ ID NO 43
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 43
agucgaauau gacgggag                                               19

<210> SEQ ID NO 44
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 44
uaugacgggg agaggaaga                                              19

<210> SEQ ID NO 45
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 45
cuguguggga cuccuaauu                                              19

<210> SEQ ID NO 46
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 46
gugggacucc uaauuacau                                              19

<210> SEQ ID NO 47
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 47
ugggacuccu aauuacaua                                              19

<210> SEQ ID NO 48
<211> LENGTH: 19

```
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 48
gacuccuaau uacauagcu                                                19

<210> SEQ ID NO 49
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 49
cuaauuacau agcucccga                                                19

<210> SEQ ID NO 50
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 50
uuacauagcu cccgaggug                                                19

<210> SEQ ID NO 51
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 51
gcaagaaagg gcacaguuu                                                19

<210> SEQ ID NO 52
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 52
gaaagggcac aguuucgag                                                19

<210> SEQ ID NO 53
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 53
ccauugggug uaucaugua                                                19

<210> SEQ ID NO 54
<211> LENGTH: 19
<212> TYPE: RNA
```

```
<213> ORGANISM: Artificial sequence
<220> FEATURE:
<223> OTHER INFORMATION: Description of Artificial Sequence: Synthetic
      oligonucleotde

<400> SEQUENCE: 54
cauugggugu aucauguau                                                    19

<210> SEQ ID NO 55
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 55
gguguaucau guauaccuu                                                    19

<210> SEQ ID NO 56
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 56
aucauguaua ccuuguuag                                                    19

<210> SEQ ID NO 57
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 57
auguauaccu uguuagugg                                                    19

<210> SEQ ID NO 58
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 58
auaccuuguu agugggcaa                                                    19

<210> SEQ ID NO 59
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 59
cuuguuagug ggcaaaacca                                                   19

<210> SEQ ID NO 60
<211> LENGTH: 19
<212> TYPE: RNA
<213> ORGANISM: Artificial sequence
```

<220> FEATURE:
<223> OTHER INFORMATION: Description of Artificial Sequence: Synthetic
      oligonucleotde

<400> SEQUENCE: 60
uuugagacuu cuugccuaa                                                19

<210> SEQ ID NO 61
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 61
agagaccuac cuccggauc                                                19

<210> SEQ ID NO 62
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 62
gagaccuacc uccggauca                                                19

<210> SEQ ID NO 63
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 63
ccuccggauc aagaagaau                                                19

<210> SEQ ID NO 64
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 64
ccggaucaag aagaaugaa                                                19

<210> SEQ ID NO 65
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 65
cggaucaaga agaaugaau                                                19

<210> SEQ ID NO 66
<211> LENGTH: 19
<212> TYPE: RNA
<213> ORGANISM: Artificial sequence
<220> FEATURE:

<223> OTHER INFORMATION: Description of Artificial Sequence: Synthetic
      oligonucleotde

<400> SEQUENCE: 66
ggaucaagaa gaaugaaua                                                    19

<210> SEQ ID NO 67
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 67
gaucaagaag aaugaauac                                                    19

<210> SEQ ID NO 68
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 68
caagaagaau gaauacagu                                                    19

<210> SEQ ID NO 69
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 69
gaagaaugaa uacaguauu                                                    19

<210> SEQ ID NO 70
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 70
gaaugaauac aguauuccc                                                    19

<210> SEQ ID NO 71
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 71
ugaauacagu auucccaag                                                    19

<210> SEQ ID NO 72
<211> LENGTH: 19
<212> TYPE: RNA
<213> ORGANISM: Artificial sequence
<220> FEATURE:
<223> OTHER INFORMATION: Description of Artificial Sequence: Synthetic oligonucleotde

<400> SEQUENCE: 72
uacaguauuc ccaagcaca                                                19

<210> SEQ ID NO 73
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 73
guauucccaa gcacaucaa                                                19

<210> SEQ ID NO 74
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 74
gaugcuucag acagauccc                                                19

<210> SEQ ID NO 75
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 75
caaccauuaa cgagcugcu                                                19

<210> SEQ ID NO 76
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 76
ccauuaacga gcugcuuaa                                                19

<210> SEQ ID NO 77
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 77
cgagcugcuu aaugacgag                                                19

<210> SEQ ID NO 78
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 78
gcuuaaugac gaguucuuu					19

<210> SEQ ID NO 79
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 79
cuuaaugacg aguucuuua					19

<210> SEQ ID NO 80
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 80
ugacgaguuc uuuacuucu					19

<210> SEQ ID NO 81
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 81
gaguucuuua cuucuggcu					19

<210> SEQ ID NO 82
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 82
guucuuuacu ucuggcuau					19

<210> SEQ ID NO 83
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 83
cuuuacuucu ggcuauauc					19

<210> SEQ ID NO 84
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

```
<400> SEQUENCE: 84
gaccauucca ccaagguuu                                                    19

<210> SEQ ID NO 85
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 85
cccucacagu ccucaauaa                                                    19

<210> SEQ ID NO 86
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 86
ccucacaguc cucaauaaa                                                    19

<210> SEQ ID NO 87
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 87
caguccucaa uaaaggcuu                                                    19

<210> SEQ ID NO 88
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 88
cucaauaaag gcuuggaga                                                    19

<210> SEQ ID NO 89
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 89
ucaauaaagg cuuggagaa                                                    19

<210> SEQ ID NO 90
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 90
```

```
caauaaaggc uuggagaac                                              19

<210> SEQ ID NO 91
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 91
uaaaggcuug gagaacccc                                              19

<210> SEQ ID NO 92
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 92
agaagaacca gugguucga                                              19

<210> SEQ ID NO 93
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 93
gaaccagugg uucgagaga                                              19

<210> SEQ ID NO 94
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 94
ccagugguuc gagagacag                                              19

<210> SEQ ID NO 95
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 95
agacagguga gguggucga                                              19

<210> SEQ ID NO 96
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 96
```
ggcaagagga ggcugagga        19

<210> SEQ ID NO 97
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 97
gcaagaggag gcugaggau        19

<210> SEQ ID NO 98
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 98
aagaggaggc ugaggaucc        19

<210> SEQ ID NO 99
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 99
ccaucuucug ggucagcaa        19

<210> SEQ ID NO 100
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 100
ucagcaagug gguggacua        19

<210> SEQ ID NO 101
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 101
cagcaagugg guggacuau        19

<210> SEQ ID NO 102
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 102
gcaagugggu ggacuauuc        19

<210> SEQ ID NO 103
<211> LENGTH: 19
<212> TYPE: RNA
<213> ORGANISM: Artificial sequence
<220> FEATURE:
<223> OTHER INFORMATION: Description of Artificial Sequence: Synthetic oligonucleotde

<400> SEQUENCE: 103
ggacuauucg gacaaguac                                              19

<210> SEQ ID NO 104
<211> LENGTH: 19
<212> TYPE: RNA
<213> ORGANISM: Artificial sequence
<220> FEATURE:
<223> OTHER INFORMATION: Description of Artificial Sequence: Synthetic oligonucleotde

<400> SEQUENCE: 104
gguaucagcu cugugauaa                                              19

<210> SEQ ID NO 105
<211> LENGTH: 19
<212> TYPE: RNA
<213> ORGANISM: Artificial sequence
<220> FEATURE:
<223> OTHER INFORMATION: Description of Artificial Sequence: Synthetic oligonucleotde

<400> SEQUENCE: 105
ggugcucuuc aaugacuca                                              19

<210> SEQ ID NO 106
<211> LENGTH: 19
<212> TYPE: RNA
<213> ORGANISM: Artificial sequence
<220> FEATURE:
<223> OTHER INFORMATION: Description of Artificial Sequence: Synthetic oligonucleotde

<400> SEQUENCE: 106
gcucuucaau gacucaaca                                              19

<210> SEQ ID NO 107
<211> LENGTH: 19
<212> TYPE: RNA
<213> ORGANISM: Artificial sequence
<220> FEATURE:
<223> OTHER INFORMATION: Description of Artificial Sequence: Synthetic oligonucleotde

<400> SEQUENCE: 107
ugacucaaca cgccucauc                                              19

<210> SEQ ID NO 108
<211> LENGTH: 19
<212> TYPE: RNA
<213> ORGANISM: Artificial sequence
<220> FEATURE:
<223> OTHER INFORMATION: Description of Artificial Sequence: Synthetic oligonucleotde

<400> SEQUENCE: 108
cacgccucau ccucuacaa                                              19

```
<210> SEQ ID NO 109
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 109
cuacaaugau ggugacagc                                                19

<210> SEQ ID NO 110
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 110
ggugacagcc ugcaguaca                                                19

<210> SEQ ID NO 111
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 111
gugacagccu gcaguacau                                                19

<210> SEQ ID NO 112
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 112
cccaacuccu ugaugaaga                                                19

<210> SEQ ID NO 113
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 113
ccaacuccuu gaugaagaa                                                19

<210> SEQ ID NO 114
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 114
acuccuugau gaagaagau                                                19
```

-continued

```
<210> SEQ ID NO 115
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 115
cuccuugaug aagaagauc                                                 19

<210> SEQ ID NO 116
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 116
gaagaagauc acccuccuu                                                 19

<210> SEQ ID NO 117
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 117
gaagaucacc cuccuuaaa                                                 19

<210> SEQ ID NO 118
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 118
gaucacccuc cuuaaauau                                                 19

<210> SEQ ID NO 119
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 119
auauuuccgc aauuacaug                                                 19

<210> SEQ ID NO 120
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 120
uuacaugagc gagcacuug                                                 19

<210> SEQ ID NO 121
```

```
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 121
gcagcgugca gaucaacuu                                                    19

<210> SEQ ID NO 122
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 122
gcgugcagau caacuucuu                                                    19

<210> SEQ ID NO 123
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 123
agaucaacuu cuuccagga                                                    19

<210> SEQ ID NO 124
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 124
gaucaacuuc uuccaggau                                                    19

<210> SEQ ID NO 125
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 125
ucaacuucuu ccaggauca                                                    19

<210> SEQ ID NO 126
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 126
cuucuuccag gaucacacc                                                    19

<210> SEQ ID NO 127
<211> LENGTH: 19
```

```
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 127
gaucacacca agcucaucu                                                    19

<210> SEQ ID NO 128
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 128
ugauggcagc cgugaccua                                                    19

<210> SEQ ID NO 129
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 129
gcagagcugc aucauccuu                                                    19

<210> SEQ ID NO 130
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 130
cccaccauau gaauuguac                                                    19

<210> SEQ ID NO 131
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 131
ccaccauaug aauuguaca                                                    19

<210> SEQ ID NO 132
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 132
caccauauga auuguacag                                                    19

<210> SEQ ID NO 133
<211> LENGTH: 19
<212> TYPE: RNA
```

```
<213> ORGANISM: Artificial sequence
<220> FEATURE:
<223> OTHER INFORMATION: Description of Artificial Sequence: Synthetic
      oligonucleotde

<400> SEQUENCE: 133
uccuuuccuu ggcuuuaug                                                   19

<210> SEQ ID NO 134
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 134
ucucuuucgc cgguggagc                                                   19

<210> SEQ ID NO 135
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 135
gagaucucga agcacuugg                                                   19

<210> SEQ ID NO 136
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 136
guccgagauc ucgaagcac                                                   19

<210> SEQ ID NO 137
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 137
uugguguccg cguccgaga                                                   19

<210> SEQ ID NO 138
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 138
agacuuaggc acaaucuug                                                   19

<210> SEQ ID NO 139
<211> LENGTH: 19
<212> TYPE: RNA
<213> ORGANISM: Artificial sequence
```

```
<220> FEATURE:
<223> OTHER INFORMATION: Description of Artificial Sequence: Synthetic
      oligonucleotde

<400> SEQUENCE: 139
cagagacuua ggcacaauc                                                    19

<210> SEQ ID NO 140
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 140
uugagcagca gagacuuag                                                    19

<210> SEQ ID NO 141
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 141
ucucccucug gugcggcuu                                                    19

<210> SEQ ID NO 142
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 142
ggauauuucc auggacauc                                                    19

<210> SEQ ID NO 143
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 143
ggugaaugga uauuuccau                                                    19

<210> SEQ ID NO 144
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 144
ugcggugaau ggauauuuc                                                    19

<210> SEQ ID NO 145
<211> LENGTH: 19
<212> TYPE: RNA
<213> ORGANISM: Artificial sequence
<220> FEATURE:
```

```
<223> OTHER INFORMATION: Description of Artificial Sequence: Synthetic
      oligonucleotde

<400> SEQUENCE: 145
ggcugcggug aauggauau                                                      19

<210> SEQ ID NO 146
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 146
aauccuacga cgugcuggu                                                      19

<210> SEQ ID NO 147
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 147
aagccgugga auccuacga                                                      19

<210> SEQ ID NO 148
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 148
aaagccgugg aauccuacg                                                      19

<210> SEQ ID NO 149
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 149
caccacgaac acgaagucg                                                      19

<210> SEQ ID NO 150
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 150
aacaccacga acacgaagu                                                      19

<210> SEQ ID NO 151
<211> LENGTH: 19
<212> TYPE: RNA
<213> ORGANISM: Artificial sequence
<220> FEATURE:
<223> OTHER INFORMATION: Description of Artificial Sequence: Synthetic
``` oligonucleotde

<400> SEQUENCE: 151
uuuccuccuc uugugcagc                                                19

<210> SEQ ID NO 152
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 152
cuuuccuccu cuugugcag                                                19

<210> SEQ ID NO 153
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 153
ucagucaggg cuuccucc                                                 19

<210> SEQ ID NO 154
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 154
uugccguagg uaguaucgg                                                19

<210> SEQ ID NO 155
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 155
uuugccguag guaguaucg                                                19

<210> SEQ ID NO 156
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 156
auuugccgua gguaguauc                                                19

<210> SEQ ID NO 157
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde -continued

<400> SEQUENCE: 157
aagcacaauu ugccguagg                                                          19

<210> SEQ ID NO 158
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 158
acuggcagcc aagcacaau                                                          19

<210> SEQ ID NO 159
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 159
uuucggugca gguacuggc                                                          19

<210> SEQ ID NO 160
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 160
uaacucgguu ucggugcag                                                          19

<210> SEQ ID NO 161
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 161
aauaacucgg uuucggugc                                                          19

<210> SEQ ID NO 162
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 162
augaauaacu cgguuucgg                                                          19

<210> SEQ ID NO 163
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 163
ucgaugaaua acucgguuu                                                    19

<210> SEQ ID NO 164
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 164
ucucgaugaa uaacucggu                                                    19

<210> SEQ ID NO 165
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 165
gaggucucga ugaauaacu                                                    19

<210> SEQ ID NO 166
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 166
uugcccagcu ugaggucuc                                                    19

<210> SEQ ID NO 167
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 167
accuccagau cuucauuca                                                    19

<210> SEQ ID NO 168
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 168
caccuccaga ucuucauuc                                                    19

<210> SEQ ID NO 169
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 169
uucaccucca gaucuucau                                          19

<210> SEQ ID NO 170
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 170
uuucaccucc agaucuuca                                          19

<210> SEQ ID NO 171
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 171
auauucgacu uugguugcc                                          19

<210> SEQ ID NO 172
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 172
ucauauucga cuuugguug                                          19

<210> SEQ ID NO 173
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 173
cgucauauuc gacuuuggu                                          19

<210> SEQ ID NO 174
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 174
ccgucauauu cgacuuugg                                          19

<210> SEQ ID NO 175
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 175
cuccccguca uauucgacu                                              19

<210> SEQ ID NO 176
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 176
ucuuccucuc cccgucaua                                              19

<210> SEQ ID NO 177
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 177
aauuaggagu cccacacag                                              19

<210> SEQ ID NO 178
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 178
auguaauuag gagucccac                                              19

<210> SEQ ID NO 179
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 179
uauguaauua ggaguccca                                              19

<210> SEQ ID NO 180
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 180
agcuauguaa uuaggaguc                                              19

<210> SEQ ID NO 181
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 181
ucgggagcua uguaauuag                                              19

<210> SEQ ID NO 182
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 182
caccucggga gcuauguaa                                             19

<210> SEQ ID NO 183
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 183
aaacugugcc cuuucuugc                                             19

<210> SEQ ID NO 184
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 184
cucgaaacug ugcccuuuc                                             19

<210> SEQ ID NO 185
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 185
uacaugauac acccaaugg                                             19

<210> SEQ ID NO 186
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 186
auacaugaua cacccaaug                                             19

<210> SEQ ID NO 187
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 187
aagguauaca ugauacacc                                             19

<210> SEQ ID NO 188
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 188
cuaacaaggu auacaugau                                                    19

<210> SEQ ID NO 189
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 189
ccacuaacaa gguauacau                                                    19

<210> SEQ ID NO 190
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 190
uugcccacua acaagguau                                                    19

<210> SEQ ID NO 191
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 191
ugguuugccc acuaacaag                                                    19

<210> SEQ ID NO 192
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 192
uuaggcaaga agucucaaa                                                    19

<210> SEQ ID NO 193
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 193
gauccggagg uaggucucu                                                    19

```
<210> SEQ ID NO 194
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 194
ugauccggag guaggucuc                                                    19

<210> SEQ ID NO 195
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 195
auucuucuug auccggagg                                                    19

<210> SEQ ID NO 196
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 196
uucauucuuc uugauccgg                                                    19

<210> SEQ ID NO 197
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 197
auucauucuu cuugauccg                                                    19

<210> SEQ ID NO 198
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 198
uauucauucu ucuugaucc                                                    19

<210> SEQ ID NO 199
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 199
guauucauuc uucuugauc                                                    19

<210> SEQ ID NO 200
```

```
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 200
acuguauuca uucuucuug                                                      19

<210> SEQ ID NO 201
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 201
aauacuguau ucauucuuc                                                      19

<210> SEQ ID NO 202
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 202
gggaauacug uauucauuc                                                      19

<210> SEQ ID NO 203
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 203
cuugggaaua cuguauuca                                                      19

<210> SEQ ID NO 204
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 204
ugugcuuggg aauacugua                                                      19

<210> SEQ ID NO 205
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 205
uugaugugcu ugggaauac                                                      19

<210> SEQ ID NO 206
<211> LENGTH: 19
```

```
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 206
gggaucuguc ugaagcauc                                                  19

<210> SEQ ID NO 207
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 207
agcagcucgu uaaugguug                                                  19

<210> SEQ ID NO 208
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 208
uuaagcagcu cguuaaugg                                                  19

<210> SEQ ID NO 209
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 209
cucgucauua agcagcucg                                                  19

<210> SEQ ID NO 210
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 210
aaagaacucg ucauuaagc                                                  19

<210> SEQ ID NO 211
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 211
uaaagaacuc gucauuaag                                                  19

<210> SEQ ID NO 212
<211> LENGTH: 19
<212> TYPE: RNA
```

```
<213> ORGANISM: Artificial sequence
<220> FEATURE:
<223> OTHER INFORMATION: Description of Artificial Sequence: Synthetic
      oligonucleotde

<400> SEQUENCE: 212
agaaguaaag aacucguca                                              19

<210> SEQ ID NO 213
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 213
agccagaagu aaagaacuc                                              19

<210> SEQ ID NO 214
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde
<220> FEATURE:
<223> OTHER INFORMATION: Description of Artificial Sequence: Synthetic
      oligonucleotde

<400> SEQUENCE: 214
auagccagaa guaaagaac                                              19

<210> SEQ ID NO 215
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 215
gauauagcca gaaguaaag                                              19

<210> SEQ ID NO 216
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 216
aaaccuuggu ggaaugguc                                              19

<210> SEQ ID NO 217
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 217
uuauugagga cugugaggg                                              19

<210> SEQ ID NO 218
```

```
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 218
uuuauugagg acugugagg                                                    19

<210> SEQ ID NO 219
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 219
aagccuuuau ugaggacug                                                    19

<210> SEQ ID NO 220
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 220
ucuccaagcc uuuauugag                                                    19

<210> SEQ ID NO 221
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 221
uucuccaagc cuuuauuga                                                    19

<210> SEQ ID NO 222
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 222
guucuccaag ccuuuauug                                                    19

<210> SEQ ID NO 223
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 223
gggguucucc aagccuuua                                                    19

<210> SEQ ID NO 224
<211> LENGTH: 19
```

```
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 224
ucgaaccacu gguucuucu                                                    19

<210> SEQ ID NO 225
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 225
ucucucgaac cacugguuc                                                    19

<210> SEQ ID NO 226
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 226
cugucucucg aaccacugg                                                    19

<210> SEQ ID NO 227
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 227
ucgaccaccu caccugucu                                                    19

<210> SEQ ID NO 228
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 228
uccucagccu ccucuugcc                                                    19

<210> SEQ ID NO 229
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 229 aucucagcc uccucuugc                                                     19

<210> SEQ ID NO 230
<211> LENGTH: 19
<212> TYPE: RNA
```

```
<213> ORGANISM: Artificial sequence
<220> FEATURE:
<223> OTHER INFORMATION: Description of Artificial Sequence: Synthetic
      oligonucleotde

<400> SEQUENCE: 230
ggauccucag ccuccucuu                                                   19

<210> SEQ ID NO 231
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 231
uugcugaccc agaagaugg                                                   19

<210> SEQ ID NO 232
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 232
uaguccaccc acuugcuga                                                   19

<210> SEQ ID NO 233
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 233
auaguccacc cacuugcug                                                   19

<210> SEQ ID NO 234
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 234
gaauagucca cccacuugc                                                   19

<210> SEQ ID NO 235
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 235
guacuugucc gaauagucc                                                   19

<210> SEQ ID NO 236
<211> LENGTH: 19
<212> TYPE: RNA
<213> ORGANISM: Artificial sequence
```

```
<220> FEATURE:
<223> OTHER INFORMATION: Description of Artificial Sequence: Synthetic
      oligonucleotde

<400> SEQUENCE: 236
uuaucacaga gcugauacc                                                    19

<210> SEQ ID NO 237
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 237
ugagucauug aagagcacc                                                    19

<210> SEQ ID NO 238
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 238
uguugaguca uugaagagc                                                    19

<210> SEQ ID NO 239
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 239
gaugaggcgu guugaguca                                                    19

<210> SEQ ID NO 240
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 240
uuguagagga ugaggcgug                                                    19

<210> SEQ ID NO 241
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 241
gcugucacca ucauuguag                                                    19

<210> SEQ ID NO 242
<211> LENGTH: 19
<212> TYPE: RNA
<213> ORGANISM: Artificial sequence
<220> FEATURE:
```

```
<223> OTHER INFORMATION: Description of Artificial Sequence: Synthetic
      oligonucleotde

<400> SEQUENCE: 242
uguacugcag gcugucacc                                                19

<210> SEQ ID NO 243
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 243
auguacugca ggcugucac                                                19

<210> SEQ ID NO 244
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 244
ucuucaucaa ggaguuggg                                                19

<210> SEQ ID NO 245
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 245
uucuucauca aggaguugg                                                19

<210> SEQ ID NO 246
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 246
aucuucuuca ucaaggagu                                                19

<210> SEQ ID NO 247
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 247
gaucuucuuc aucaaggag                                                19

<210> SEQ ID NO 248
<211> LENGTH: 19
<212> TYPE: RNA
<213> ORGANISM: Artificial sequence
<220> FEATURE:
<223> OTHER INFORMATION: Description of Artificial Sequence: Synthetic
``` oligonucleotde

<400> SEQUENCE: 248
aaggagggug aucuucuuc                                            19

<210> SEQ ID NO 249
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 249
uuuaaggagg gugaucuuc                                            19

<210> SEQ ID NO 250
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 250
auauuuaagg agggugauc                                            19

<210> SEQ ID NO 251
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 251
cauguaauug cggaaauau                                            19

<210> SEQ ID NO 252
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 252
caagugcucg cucauguaa                                            19

<210> SEQ ID NO 253
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 253
aaguugaucu gcacgcugc                                            19

<210> SEQ ID NO 254
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

```
<400> SEQUENCE: 254
aagaaguuga ucugcacgc                                                    19

<210> SEQ ID NO 255
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 255
uccuggaaga aguugaucu                                                    19

<210> SEQ ID NO 256
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 256
auccuggaag aaguugauc                                                    19

<210> SEQ ID NO 257
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 257
ugauccugga agaaguuga                                                    19

<210> SEQ ID NO 258
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 258
ggugugaucc uggaagaag                                                    19

<210> SEQ ID NO 259
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 259
agaugagcuu ggugugauc                                                    19

<210> SEQ ID NO 260
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde
```

<400> SEQUENCE: 260
uaggucacgg cugccauca					19

<210> SEQ ID NO 261
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 261
aaggaugaug cagcucugc					19

<210> SEQ ID NO 262
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 262
guacaauuca uaugguggg					19

<210> SEQ ID NO 263
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 263
uguacaauuc auauggugg					19

<210> SEQ ID NO 264
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 264
cuguacaauu cauauggug					19

<210> SEQ ID NO 265
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotde

<400> SEQUENCE: 265
cauaaagcca aggaaagga					19

<210> SEQ ID NO 266
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotde
<220> FEATURE:
<223> OTHER INFORMATION: Synthesized Primer -continued
<210> SEQ ID NO 267
<211> LENGTH: 20
<212> TYPE: DNA
<213> ORGANISM: Artificial sequence
<220> FEATURE:
<223> OTHER INFORMATION: Synthesized Primer

<400> SEQUENCE: 267
tacccaaggc cgtacttgtc                                               20

<210> SEQ ID NO 268
<211> LENGTH: 20
<212> TYPE: DNA
<213> ORGANISM: Artificial sequence
<220> FEATURE:
<223> OTHER INFORMATION: Synthesized Primer

<400> SEQUENCE: 268
agcgagcatc ccccaaagtt                                               20

<210> SEQ ID NO 269
<211> LENGTH: 20
<212> TYPE: DNA
<213> ORGANISM: Artificial sequence
<220> FEATURE:
<223> OTHER INFORMATION: Synthesized Primer

<400> SEQUENCE: 269
gggcacgaag gctcatcatt                                               20

<210> SEQ ID NO 270
<211> LENGTH: 21
<212> TYPE: DNA
<213> ORGANISM: Artificial sequence
<220> FEATURE:
<223> OTHER INFORMATION: Sense strand of synthesized siRNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (19)..(19)
<223> OTHER INFORMATION: 2'-O-methyladenosine

<400> SEQUENCE: 270
ggaucaagaa gaaugaauat t                                             21

<210> SEQ ID NO 271
<211> LENGTH: 21
<212> TYPE: DNA
<213> ORGANISM: Artificial sequence
<220> FEATURE:

<223> OTHER INFORMATION: Antisense strand of synthesized siRNA
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (15)..(15)
<223> OTHER INFORMATION: gm

<400> SEQUENCE: 271
uauucauucu ucuugaucct t                              21

<210> SEQ ID NO 272
<211> LENGTH: 21
<212> TYPE: DNA
<213> ORGANISM: Artificial sequence
<220> FEATURE:
<223> OTHER INFORMATION: Sense strand of synthesized siRNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (18)..(18)
<223> OTHER INFORMATION: um

<400> SEQUENCE: 272
ggaucaagaa gaaugaauat t                              21

<210> SEQ ID NO 273
<211> LENGTH: 21
<212> TYPE: DNA
<213> ORGANISM: Artificial sequence
<220> FEATURE:
<223> OTHER INFORMATION: Antisense strand of synthesized siRNA
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-flurocytidine
<220> FEATURE:
<221> NAME/KEY: modified_base
<222> LOCATION: (17)..(17)
<223> OTHER INFORMATION: 2'-flurouridine

<400> SEQUENCE: 273
uauucauucu ucuugaucct t                              21

<210> SEQ ID NO 274
<211> LENGTH: 21
<212> TYPE: DNA
<213> ORGANISM: Artificial sequence
<220> FEATURE:
<223> OTHER INFORMATION: Sense strand of synthesized siRNA
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: cm

<400> SEQUENCE: 274
caagaagaau gaauacagut t                                              21

<210> SEQ ID NO 275
<211> LENGTH: 21
<212> TYPE: DNA
<213> ORGANISM: Artificial sequence
<220> FEATURE:
<223> OTHER INFORMATION: Antisense strand of synthesized siRNA
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (18)..(18)
<223> OTHER INFORMATION: 2'-flurouridine

<400> SEQUENCE: 275
acuguauuca uucuucuugt t                                              21

<210> SEQ ID NO 276
<211> LENGTH: 21
<212> TYPE: DNA
<213> ORGANISM: Artificial sequence
<220> FEATURE:
<223> OTHER INFORMATION: Sense strand of synthesized siRNA
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-O-methyladenosine

<400> SEQUENCE: 276
caagaagaau gaauacagut t                                              21

```
<210> SEQ ID NO 277
<211> LENGTH: 21
<212> TYPE: DNA
<213> ORGANISM: Artificial sequence
<220> FEATURE:
<223> OTHER INFORMATION: Antisense strand of synthesized siRNA
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-flurouridine
<220> FEATURE:
<221> NAME/KEY: modified_base
<222> LOCATION: (18)..(18)
<223> OTHER INFORMATION: 2'-flurouridine

<400> SEQUENCE: 277
acuguauuca uucuucuugt t                                              21

<210> SEQ ID NO 278
<211> LENGTH: 21
<212> TYPE: DNA
<213> ORGANISM: Artificial sequence
<220> FEATURE:
<223> OTHER INFORMATION: Sense strand of synthesized siRNA
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (14)..(14)
<223> OTHER INFORMATION: gm

<400> SEQUENCE: 278
cgagcugcuu aaugacgagt t                                              21

<210> SEQ ID NO 279
<211> LENGTH: 21
<212> TYPE: DNA
<213> ORGANISM: Artificial sequence
<220> FEATURE:
<223> OTHER INFORMATION: Antisense strand of synthesized siRNA
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (6)..(6)
<223> OTHER INFORMATION: 2'-flurocytidine

<400> SEQUENCE: 279
cucgucauua agcagcucgt t                                              21

<210> SEQ ID NO 280
<211> LENGTH: 21
<212> TYPE: DNA
<213> ORGANISM: Artificial sequence
<220> FEATURE:
<223> OTHER INFORMATION: Sense strand of control siRNA

<400> SEQUENCE: 280
uucuccgaac gugucacgut t                                              21
```

```
<210> SEQ ID NO 281
<211> LENGTH: 21
<212> TYPE: DNA
<213> ORGANISM: Artificial sequence
<220> FEATURE:
<223> OTHER INFORMATION: Sense strand of control siRNA

<400> SEQUENCE: 281
acgugacacg uucggagaat t                                              21
```